US011859179B2

(12) United States Patent
Mueller et al.

(10) Patent No.: US 11,859,179 B2
(45) Date of Patent: Jan. 2, 2024

(54) METHODS OF TREATING AMYOTROPHIC LATERAL SCLEROSIS (ALS)

(71) Applicant: University of Massachusetts, Boston, MA (US)

(72) Inventors: Christian Mueller, Concord, MA (US); Abbas Abdallah, Worcester, MA (US)

(73) Assignee: University of Massachusetts, Boston, MA (US)

(*) Notice: Subject to any disclaimer, the term of this patent is extended or adjusted under 35 U.S.C. 154(b) by 696 days.

(21) Appl. No.: 16/611,581

(22) PCT Filed: May 9, 2018

(86) PCT No.: PCT/US2018/031880
§ 371 (c)(1),
(2) Date: Nov. 7, 2019

(87) PCT Pub. No.: WO2018/208972
PCT Pub. Date: Nov. 15, 2018

(65) Prior Publication Data
US 2020/0354716 A1  Nov. 12, 2020

Related U.S. Application Data

(60) Provisional application No. 62/503,909, filed on May 9, 2017.

(51) Int. Cl.
| C12N 15/861 | (2006.01) |
| C12N 15/11 | (2006.01) |
| A61K 35/76 | (2015.01) |
| C12N 9/22 | (2006.01) |
| C12N 15/86 | (2006.01) |
| C12N 15/90 | (2006.01) |

(52) U.S. Cl.
CPC .............. *C12N 15/11* (2013.01); *A61K 35/76* (2013.01); *C12N 9/22* (2013.01); *C12N 15/86* (2013.01); *C12N 15/8616* (2013.01); *C12N 15/907* (2013.01); *C12N 2310/20* (2017.05); *C12N 2750/14143* (2013.01); *C12N 2750/14171* (2013.01); *C12N 2800/80* (2013.01)

(58) Field of Classification Search
CPC .......... C12N 15/11; C12N 9/22; C12N 15/86; C12N 15/907; C12N 2310/20; C12N 2750/14143; C12N 2750/14171; C12N 2800/80; A61K 35/76
See application file for complete search history.

(56) References Cited

U.S. PATENT DOCUMENTS

| 5,478,745 A | 12/1995 | Samulski et al. |
| 5,871,982 A | 2/1999 | Wilson et al. |
| 6,001,650 A | 12/1999 | Colosi |
| 6,156,303 A | 12/2000 | Russell et al. |
| 6,177,403 B1 | 1/2001 | Stedman |
| 6,251,677 B1 | 6/2001 | Wilson et al. |
| 6,485,966 B2 | 11/2002 | Gao et al. |
| 6,544,786 B1 | 4/2003 | Xiao et al. |
| 6,953,690 B1 | 10/2005 | Gao et al. |
| 7,022,519 B2 | 4/2006 | Gao et al. |
| 7,132,530 B2 | 11/2006 | Bennett et al. |
| 7,198,951 B2 | 4/2007 | Gao et al. |
| 7,235,393 B2 | 6/2007 | Gao et al. |
| 7,387,896 B2 | 6/2008 | Turner et al. |
| 7,427,396 B2 | 9/2008 | Arbetman et al. |
| 7,456,015 B2 | 11/2008 | Bohn et al. |
| 7,498,316 B2 | 3/2009 | Xu et al. |
| 7,622,455 B2 | 11/2009 | Bennett et al. |
| 7,678,895 B2 | 3/2010 | Bennett et al. |
| 7,691,995 B2 | 4/2010 | Zamore et al. |
| 7,750,144 B2 | 7/2010 | Zamore et al. |
| 7,772,203 B2 | 8/2010 | Zamore et al. |
| 7,892,793 B2 | 2/2011 | Xu |
| 7,902,163 B2 | 3/2011 | Bennett et al. |
| 7,906,111 B2 | 3/2011 | Wilson et al. |
| 8,008,271 B2 | 8/2011 | Xu et al. |
| 8,202,846 B2 | 6/2012 | Hannon et al. |
| 8,222,221 B2 | 7/2012 | Corey et al. |
| 8,309,533 B2 | 11/2012 | Xu |
| 8,524,446 B2 | 9/2013 | Gao et al. |
| 8,729,036 B2 | 5/2014 | Zamore et al. |
| 8,734,809 B2 | 5/2014 | Gao et al. |
| 8,993,529 B2 | 3/2015 | Bennett et al. |
| 9,102,949 B2 | 8/2015 | Gao et al. |
| 9,121,018 B2 | 9/2015 | Zamore et al. |
| 9,193,753 B2 | 11/2015 | Tuschl et al. |
| 9,217,155 B2 | 12/2015 | Gao et al. |
| 9,226,976 B2 | 1/2016 | Flotte et al. |
| 9,249,424 B2 | 2/2016 | Wolf et al. |
| 9,272,053 B2 | 3/2016 | Gao et al. |
| 9,284,357 B2 | 3/2016 | Gao et al. |
| 9,546,369 B2 | 1/2017 | Gao et al. |
| 9,596,835 B2 | 3/2017 | Gao et al. |
| 9,611,472 B2 | 4/2017 | Zamore et al. |
| 9,701,984 B2 | 7/2017 | Gao et al. |
| 9,850,487 B2 | 12/2017 | Zamore et al. |
| 9,879,253 B2 | 1/2018 | Zamore et al. |

(Continued)

FOREIGN PATENT DOCUMENTS

| JP | 2011-511636 A | 4/2011 |
| JP | 2017-510298 A | 4/2017 |

(Continued)

OTHER PUBLICATIONS

Pribadi et al. in (bioRxiv; available online May 2, 2016.). (Year: 2016).*

(Continued)

*Primary Examiner* — Catherine S Hibbert
(74) *Attorney, Agent, or Firm* — Wolf, Greenfield & Sacks, P.C.

(57) ABSTRACT

Aspects of the disclosure relate to recombinant gene editing complexes comprising a recombinant gene editing protein and guide RNA (gRNA) that specifically hybridizes to a region of a C9ORF72 gene (e.g., a region flanking a $G_4C_2$ repeat or within a exonic region of the gene).

9 Claims, 21 Drawing Sheets

Specification includes a Sequence Listing.

(56) References Cited

U.S. PATENT DOCUMENTS

| | | |
|---|---|---|
| 9,885,057 B2 | 2/2018 | Flotte et al. |
| 10,072,251 B2 | 9/2018 | Gao et al. |
| 10,077,452 B2 | 9/2018 | Flotte et al. |
| 10,166,297 B2 | 1/2019 | Gao et al. |
| 10,280,418 B2 | 5/2019 | Mueller et al. |
| 10,300,146 B2 | 5/2019 | Gao et al. |
| 10,370,432 B2 | 8/2019 | Esteves et al. |
| 10,597,656 B2 | 3/2020 | Flotte et al. |
| 10,711,274 B2 | 7/2020 | Mueller et al. |
| 10,793,861 B2 | 10/2020 | Kaspar et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2004/0101514 A1 | 5/2004 | Liu et al. |
| 2004/0219528 A1 | 11/2004 | Morris et al. |
| 2005/0014262 A1 | 1/2005 | Gao et al. |
| 2005/0019915 A1 | 1/2005 | Bennett et al. |
| 2005/0032219 A1 | 2/2005 | Aubourg et al. |
| 2005/0037988 A1 | 2/2005 | Zamore et al. |
| 2005/0137153 A1 | 6/2005 | McSwiggen et al. |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0255487 A1 | 11/2005 | Khvorova et al. |
| 2005/0261218 A1 | 11/2005 | Esau et al. |
| 2005/0287122 A1 | 12/2005 | Bartlett et al. |
| 2005/0288243 A1 | 12/2005 | Xu et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0229268 A1 | 10/2006 | Benjamin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2007/0253936 A1 | 11/2007 | Kay et al. |
| 2007/0292410 A1 | 12/2007 | Cashman et al. |
| 2008/0200420 A1 | 8/2008 | Zamore et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0215879 A1 | 8/2009 | DiPrimio et al. |
| 2009/0239240 A1 | 9/2009 | Chu |
| 2010/0186103 A1 | 7/2010 | Gao et al. |
| 2010/0323001 A1 | 12/2010 | Pachuk |
| 2011/0039914 A1 | 2/2011 | Pavco et al. |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0281516 A1 | 10/2013 | Gao et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0296486 A1 | 10/2014 | Gao et al. |
| 2014/0335054 A1 | 11/2014 | Gao et al. |
| 2015/0065560 A1 | 3/2015 | Bjorklund et al. |
| 2015/0252421 A1 | 9/2015 | Pickering-Brown et al. |
| 2015/0258180 A1 | 9/2015 | Mahuran et al. |
| 2015/0259679 A1 | 9/2015 | Bennett et al. |
| 2016/0017005 A1 | 1/2016 | Asokan et al. |
| 2016/0024496 A1 | 1/2016 | Bennett et al. |
| 2016/0060624 A1 | 3/2016 | Davidson et al. |
| 2016/0076054 A1 | 3/2016 | Auricchio et al. |
| 2016/0135438 A1 | 5/2016 | Gao et al. |
| 2016/0153005 A1 | 6/2016 | Zhang et al. |
| 2016/0185832 A1 | 6/2016 | Drivas et al. |
| 2016/0186211 A1 | 6/2016 | Flotte et al. |
| 2016/0194374 A1 | 7/2016 | Wijnholds et al. |
| 2016/0208257 A1 | 7/2016 | Gao et al. |
| 2016/0251655 A1 | 9/2016 | Freier et al. |
| 2016/0272976 A1 | 9/2016 | Kaspar |
| 2016/0326524 A1 | 11/2016 | Flotte et al. |
| 2017/0029785 A1 | 2/2017 | Zhao et al. |
| 2017/0101645 A1 | 4/2017 | Brown et al. |
| 2017/0114340 A1 | 4/2017 | Mueller et al. |
| 2017/0145439 A1 | 5/2017 | Gao et al. |
| 2017/0152517 A1 | 6/2017 | Barkats et al. |
| 2017/0159071 A9 | 6/2017 | Flotte et al. |
| 2017/0165377 A1 | 6/2017 | Gao et al. |
| 2017/0166927 A1 | 6/2017 | Gao et al. |
| 2017/0191039 A1 | 7/2017 | Gao et al. |
| 2017/0349911 A1 | 12/2017 | Gao et al. |
| 2018/0094267 A1* | 4/2018 | Heslin ................. C12N 15/113 |
| 2018/0140810 A1 | 5/2018 | Cataltepe et al. |
| 2018/0214576 A1 | 8/2018 | Fitzgerald et al. |
| 2018/0265571 A1 | 9/2018 | Esteves et al. |
| 2018/0265863 A1 | 9/2018 | Esteves et al. |
| 2018/0265865 A2 | 9/2018 | Flotte et al. |
| 2018/0298380 A1 | 10/2018 | Gao et al. |
| 2018/0311290 A1 | 11/2018 | Sena-Esteves et al. |
| 2019/0211327 A1 | 7/2019 | Flotte et al. |
| 2019/0276826 A1 | 9/2019 | Mueller et al. |
| 2019/0282709 A1 | 9/2019 | Gao et al. |
| 2019/0316126 A1 | 10/2019 | Mueller et al. |
| 2020/0032256 A1 | 1/2020 | Mueller et al. |
| 2020/0248187 A1 | 8/2020 | Mueller et al. |
| 2021/0246450 A1 | 8/2021 | Mueller et al. |

FOREIGN PATENT DOCUMENTS

| | | |
|---|---|---|
| JP | 2018-538002 A | 12/2018 |
| WO | WO 2003/006477 A1 | 1/2003 |
| WO | WO 2003/042397 A2 | 5/2003 |
| WO | WO 2005/033321 A2 | 4/2005 |
| WO | WO 2005/062937 A2 | 7/2005 |
| WO | WO 2005/116204 A1 | 12/2005 |
| WO | WO 2006/031267 A2 | 3/2006 |
| WO | WO 2006/066066 A2 | 6/2006 |
| WO | WO 2006/119432 A2 | 11/2006 |
| WO | WO 2007/000668 A2 | 1/2007 |
| WO | WO 2007/027775 A2 | 3/2007 |
| WO | WO 2008/091703 A2 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/102427 A2 | 8/2009 |
| WO | WO 2009/109665 A1 | 9/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2011/133890 A1 | 10/2011 |
| WO | WO 2011/135396 A1 | 11/2011 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/062691 A2 | 4/2014 |
| WO | WO 2014/114303 A1 | 7/2014 |
| WO | WO 2014/160092 A1 | 10/2014 |
| WO | WO 2014/186746 A1 | 11/2014 |
| WO | WO 2014/197748 A2 | 12/2014 |
| WO | WO 2015/031392 A1 | 3/2015 |
| WO | WO 2015/054676 A2 | 4/2015 |

(56) References Cited

FOREIGN PATENT DOCUMENTS

| | | |
|---|---|---|
| WO | WO 2015/057727 A1 | 4/2015 |
| WO | WO 2015/089354 A1 | 6/2015 |
| WO | WO 2015/121501 A1 | 8/2015 |
| WO | WO 2015/143078 A1 | 9/2015 |
| WO | WO 2015/164786 A1 | 10/2015 |
| WO | WO 2015/168666 A2 | 11/2015 |
| WO | WO 2015/195621 A1 | 12/2015 |
| WO | WO 2016/065001 A1 | 4/2016 |
| WO | WO 2016/112132 A1 | 7/2016 |
| WO | WO 2016/167780 A1 | 10/2016 |
| WO | WO 2016/174056 A1 | 11/2016 |
| WO | WO 2016/186772 A2 | 11/2016 |
| WO | WO 2016/187053 A1 | 11/2016 |
| WO | WO 2016/210372 A2 | 12/2016 |
| WO | WO-2016210372 A2 * 12/2016 ............ A61K 31/27 |
| WO | WO 2017/023724 A1 | 2/2017 |
| WO | WO 2017/109757 A1 | 6/2017 |
| WO | WO-2017109757 A1 * 6/2017 ........... A61K 31/395 |
| WO | WO 2018/064600 A1 | 4/2018 |

OTHER PUBLICATIONS

Lisowski et al.("Adeno-associated virus serotypes for gene therapeutics" Current opinion in pharmacology vol. 24, No. 59; Oct. 2015). (Year: 2015).*

Hinderer et al in "Widespread gene transfer in the central nervous system of cynomolgus macaques following delivery of AAV9 into the cisterna magna" (Molecular Therapy—Methods & Clinical Development (2014 vol. 1,, pp. 1-9). (Year: 2014).*

Gaj et al Genome Engineering Using Adeno-associated Virus: Basic and Clinical Research Applications. Molecular therapy: the journal of the American Society of Gene Therapy, Sep. 16, 2015). (Year: 2015).*

Cleary in "Effect of C9orf72 hexanucleotide repeat expansions on human induced pluripotent stem cell derived oligodendrocytes" (Cleary PhD Dissertation, The University of Edinburgh, Jan. 12, 2017). (Year: 2017).*

Pinto et al "Impeding Transcription of Expanded Microsatellite Repeats by Deactivated Cas9" (Molecular Cell vol. 68, Nov. 2, 2017, pp. 479-490). (Year: 2017).*

Sirninger et al.(Human Gene Therapy vol. 15: pp. 832-841, Sep. 2004). (Year: 2004).*

Abdallah & Mueller in "Gene editing ALS causing (GGGGCC)n repeat expansion in C9orf72 using CRISPER/Cas9 system" (Molecular Therapy, suppl. Supplement 1 vol. 25, No. 5: pp. 299-300. American Society of Gene and Cell Therapy. May 2017). (Year: 2017).*

Extended European Search Report for Application No. EP 15764861.9, dated Dec. 15, 2017.

International Search Report and Written Opinion for Application No. PCT/US2015/021321, dated Jun. 26, 2015.

International Preliminary Report on Patentability for Application No. PCT/US2015/021321, dated Sep. 26, 2016.

International Search Report and Written Opinion for Application No. PCT/US2018/031880, dated Sep. 14, 2018.

International Preliminary Report on Patentability for Application No. PCT/US2018/031880, dated Nov. 21, 2019.

International Search Report and Written Opinion for Application No. PCT/US2018/052173, dated Nov. 30, 2018.

International Preliminary Report on Patentability for Application No. PCT/US2018/052173, dated Apr. 2, 2020.

Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

Adachi et al., Drawing a high-resolution functional map of adeno-associated virus capsid by massively parallel sequencing. Nat Commun. 2014;5:3075. doi: 10.1038/ncomms4075.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Alisky et al., Gene therapy for amyotrophic lateral sclerosis and other motor neuron diseases. Hum Gene Ther. Nov. 20, 2000;11(17):2315-29.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Azzouz et al., VEGF delivery with retrogradely transported lentivector prolongs survival in a mouse ALS model. Nature. May 27, 2004;429(6990):413-7.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Banci et al., SOD1 and amyotrophic lateral sclerosis: mutations and oligomerization. PLoS One. 2008;3(2):e1677. Published Feb. 27, 2008. doi:10.1371/journal.pone.0001677.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Biferi et al., Recombinant AAV9 vectors to silence the mutant SOD1 gene in amyotrophic lateral sclersosis. Human gene therapy. Dec. 2013;24(12):A117.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Boillée et al., Onset and progression in inherited ALS determined by motor neurons and microglia. Science. Jun. 2, 2006;312(5778):1389-92.

Borel et al., Recombinant AAV as a platform for translating the therapeutic potential of RNA interference. Mol Ther. Apr. 2014;22(4):692-701. doi:10.1038/mt.2013.285. Epub Dec. 19, 2013.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.

Brown et al., A microRNA-regulated lentiviral vector mediates stable correction of hemophilia B mice. Blood. Dec. 15, 2007;110(13):4144-52. Epub Aug. 28, 2007.

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006;12(5):585-91. Epub Apr. 23, 2006.

Buning et al., Receptor targeting of adeno-associated virus vectors. Gene Ther. Jul. 2003;10(14):1142-51.

Bussing et al., let-7 microRNAs in development, stem cells and cancer. Trends Mol Med. Sep. 2008;14(9):400-9. doi: 10.1016/j.molmed.2008.07.001. Epub Jul. 31, 2008.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

(56) References Cited

OTHER PUBLICATIONS

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Chen et al., Regulation of immune responses and tolerance: the microRNA perspective. Immunol Rev. May 2013;253(1):112-28. doi:10.1111/imr.12060.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Choudhury et al., Identification of Novel vectors capable of CNS transduction in adult mice after single round selection using DNA shuffled AAV capsid library. Mol Ther. May 1, 2013;21(1):S1.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Chung et al., Polycistronic RNA polymerase II expression vectors for RNA interference based on BIC/miR-155. Nucleic Acids Res. Apr. 13, 2006;34(7):e53.
Conlon et al., Ribozyme Approaches towards Down-Regulation of Pi*Z Mutant Human a-1 Anti-Trypsin. Mol. Therapy. 2004;9:S333. Abstract 875.
Conrad et al., Safety of single-dose administration of an adeno-associated virus (AAV)-CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Cruz et al., The promise of gene therapy for the treatment of alpha-1 antitrypsin deficiency. Pharmacogenomics. Sep. 2007;8(9):1191-8.
Csak et al., microRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.
Czech, MicroRNAs as therapeutic targets. N Engl J Med. Mar. 16, 2006;354(11):1194-5.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.
Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015. Erratum in: Neuron. Nov. 20, 2013;80(4):1102. Heusler, Aaron R [corrected to Haeusler, Aaron R].
Donnelly et al., RNA toxicity from the ALS/FTD C9ORF72 expansion is mitigated by antisense intervention. Neuron. Oct. 16, 2013;80(Supplemental Information). 33 pages.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Eberling et al., Results from a phase I safety trial of hAADC gene therapy for Parkinson disease. Neurology. May 2 2008;70(21):1980-3. doi: 10.1212/01.wnl.0000312381.29287.ff. Epub Apr. 9, 2008.
Ebert et al., MicroRNA sponges: competitive inhibitors of small RNAs in mammalian cells. Nat Methods. Sep. 2007;4(9):721-6. Epub Aug. 12, 2007.
Ehlert et al., Cellular toxicity following application of adeno-associated viral vector-mediated RNA interference in the nervous system. BMC Neurosci. Feb. 18, 2010;11:20.
Elmén et al., LNA-mediated microRNA silencing in non-human primates. Nature. Apr. 2008;452(17): 896-900.
Elmén et al.,bAntagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes. Nature Biotechnology, 27; 59-65 2009.
Foust et al., Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

(56) References Cited

OTHER PUBLICATIONS

Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi: 10.1038/mt.2012.200. Epub Sep. 25, 2012.
Gao et al., Erythropoietin gene therapy leads to autoimmune anemia in macaques. Blood. May 1, 2004;103(9):3300-2. Epub Dec. 24, 2003.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
Genbank Submission; NCBI, Accession No. AAS99264; Gao et al.; Jun. 24, 2004.
Genbank Submission; NCBI, Accession No. AY530579.10; 2004.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Georgiadis et al., AAV-mediated knockdown of peripherin-2 in vivo using miRNA-based hairpins. Gene Ther. Apr. 2010;17(4):486-93. doi: 10.1038/gt.2009.162. Epub Dec. 10, 2009.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Gramantieri et al., Cyclin G1 is a target of miR-122a, a microRNA frequently down-regulated in human hepatocellular carcinoma. Cancer Res. Jul. 1, 2007;67(13):6092-9.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Haussecker et al., miR-122 continues to blaze the trail for microRNA therapeutics. Mol Ther. Feb. 2010;18(2):240-2. doi: 10.1038/mt.2009.313.
Hernandez et al., Latent adeno-associated virus infection elicits humoral but not cell-mediated immune responses in a nonhuman primate host. J Virol. Oct. 1999; 73(10):8549-58.
Horwich et al., Design and delivery of antisense oligonucleotides to block microRNA function in cultured *Drosophila* and human cells. Nat Protoc. 2008;3(10):1537-49. doi: 10.1038/nprot.2008.145.
Hsu et al., Essential metabolic, anti-inflammatory, and anti-tumorigenic functions of miR-122 in liver. J Clin Invest. Aug. 2012;122(8):2871-83. doi: 10.1172/JCI63539. Epub Jul. 23, 2012.
Hutvágner et al., Sequence-specific inhibition of small RNA function. PLoS Biol. Apr. 2004;2(4):E98. Epub Feb. 24, 2004.
Iida et al., Systemic Delivery of Tyrosine-Mutant AAV Vectors Results in Robust Transduction of Neurons in Adult Mice. BioMed Res Int. 2013;2013.
Jakobsson et al., Lentiviral vectors for use in the central nervous system. Mol Ther. Mar. 2006;13(3):484-93. Epub Jan. 3, 2006.
Johnson et al., RAS is regulated by the let-7 microRNA family. Cell. Mar. 11, 2005;120(5):635-47.
Kaspar et al., Retrograde viral delivery of IGF-1 prolongs survival in a mouse ALS model. Science. Aug. 8, 2003;301(5634):839-42.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Kotin et al., Organization of adeno-associated virus DNA in latently infected Detroit 6 cells. Virology. Jun. 1989; 170(2):460-7.
Kotin et al., Site-specific integration by adeno-associated virus. Proc Natl Acad Sci U S A. Mar. 1990;87(6):2211-5.
Krützfeldt et al., Silencing of microRNAs in vivo with 'antagomirs'. Nature. Dec. 1, 2005;438(7068):685-9. Epub Oct. 30, 2005.
Kutay et al., Downregulation of miR-122 in the rodent and human hepatocellular carcinomas. J Cell Biochem. Oct. 15, 2006;99(3):671-8.
Lanford et al., Therapeutic silencing of microRNA-122 in primates with chronic hepatitis C virus infection. Science. Jan. 8, 2010;327(5962):198-201. Epub Dec. 3, 2009.
Lewis et al., Conserved seed pairing, often flanked by adenosines, indicates that thousands of human genes are microRNA targets. Cell. Jan. 14, 2005;120(1):15-20.
Lewis et al., Prediction of mammalian microRNA targets. Cell. Dec. 26, 2003;115(7):787-98.
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Intronic microRNA: discovery and biological implications. DNA Cell Biol. Apr. 2007;26(4):195-207.
Li et al., Protein trans-splicing as a means for viral vector-mediated in vivo gene therapy. Hum Gene Ther. Sep. 2008;19(9):958-64. doi: 10.1089/hum.2008.009.
Liu et al., Altered microRNA expression following traumatic spinal cord injury. Exp Neurol. Oct. 2009;219(2):424-9. doi: 10.1016/j.expneurol.2009.06.015. Epub Jul. 1, 2009.
Liu et al., Identification of a novel loss-of-function C9orf72 splice site mutation in a patient with amyotrophic lateral sclerosis. Neurobiol Aging. Nov. 2016;47:219.e1-219.e5. doi: 10.1016/j.neurobiolaging.2016.07.027. Epub Aug. 8, 2016.
Lowenstein, Crossing the rubicon. Nat Biotechnol. Jan. 2009;27(1):42-4.
Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.
Lux et al., Green fluorescent protein-tagged adeno-associated virus particles allow the study of cytosolic and nuclear trafficking. J Virol. Sep. 2005;79(18):11776-87.
Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Mandel et al., Recombinant adeno-associated viral vectors as therapeutic agents to treat neurological disorders. Mol Ther. Mar. 2006;13(3):463-83. Epub Jan. 18, 2006.
Manfredsson et al., AAV9: a potential blood-brain barrier buster. Mol Ther. Mar. 2009;17(3):403-5.
Matalon et al., Adeno-associated virus-mediated aspartoacylase gene transfer to the brain of knockout mouse for canavan disease. Mol Ther. May 2003;7(5 Pt 1):580-7.

(56) References Cited

OTHER PUBLICATIONS

McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Meister et al., Sequence-specific inhibition of microRNA- and siRNA-induced RNA silencing. RNA. Mar. 2004;10(3):544-50.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi: 10.1089/hum.2015.050. Epub Aug. 6, 2015.
MiRBase accession No. MI0000472. Last accessed on May 18, 2018 at http://www.mirbase.org/cgi-bin/mirna_entry.pl?acc=MI0000472.
Moffett et al., N-Acetylaspartate in the CNS: from neurodiagnostics to neurobiology. Prog Neurobiol. Feb. 2007;81(2):89-131. Epub Jan. 5, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., Using rAAV Delivered miRNAs To Knockdown Misfolded Human Alpha 1 Antitrypsin in a Transgenic Mouse Model. Molecular Therapy May 2010;18(1):S21. Abstract 51.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Pribadi et al., CRISPR-Cas9 targeted deletion of the C9orf72 repeat expansion mutation corrects cellular phenotypes in patient-derived iPS cells. Preprint published May 2, 2016.
Ralph et al., Silencing mutant SOD1 using RNAi protects against neurodegeneration and extends survival in an ALS model. Nat Med. Apr. 2005;11(4):429-33. Epub Mar. 13, 2005.
Ran et al., In vivo genome editing using *Staphylococcus aureus* Cas9. Nature. Apr. 9, 2015;520(7546):186-91. doi: 10.1038/nature14299. Epub Apr. 1, 2015.
Raoul et al., Lentiviral-mediated silencing of SOD1 through RNA interference retards disease onset and progression in a mouse model of ALS. Nat Med. Apr. 2005;11(4):423-8. Epub Mar. 13, 2005.
Renton et al., State of play in amyotrophic lateral sclerosis genetics. Nat Neurosci. 2014;17(1):17-23. doi:10.1038/nn.3584.
Sambrook et al., "Molecular Cloning. A Laboratory Manual", 2d ed., Cold Spring Harbor Laboratory, New York (1989).
Schnepp et al., Characterization of adeno-associated virus genomes isolated from human tissues. J Virol. Dec. 2005; 79(23):14793-803.
Sen et al., Micromanaging vascular biology: tiny microRNAs play big band. J Vasc Res. 2009;46(6):527-40. doi: 10.1159/000226221. Epub Jun. 30, 2009.
Sin et al., Gene silencing efficiency and INF-? induction effects of splicing miRNA 155-based artificial miRNA with pre-miRNA stem-loop structures. Biochem Genet. Feb. 2012;50(1-2):112-21. doi: 10.1007/s10528-011-9476-y. Epub Nov. 27, 2011.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh. 10 rhesus macaque-derived adeno-associated virus vector. Mol Ther. Mar. 2007;15(3):481-91. Epub Dec. 19, 2006.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Suckau et al., 851. The Effect of Genome Size and Design of scAAV Vectors on Efficiency of shRNA Expression and Gene Knockdown. May 1, 2007;15(1):S325.
Tanimizu et al., Downregulation of miR122 by grainyhead-like 2 restricts the hepatocytic differentiation potential of adult liver progenitor cells. Development. Dec. 2014;141(23):4448-56. doi:10.1242/dev.113654. Epub Nov. 18, 2014.
Tenenbaum et al., Recombinant AAV-mediated gene delivery to the central nervous system. J Gene Med. Feb. 2004;6 Suppl 1:S212-22.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008; 16(6):1018-25. doi: 10. 1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
U.S. Appl. No. 15/098,833, filed Apr. 14, 2016, Flotte et al.
U.S. Appl. No. 15/120,294, filed Aug. 19, 2016, Gao et al.
U.S. Appl. No. 15/316,027, filed Dec. 2, 2016, Brown et al.
U.S. Appl. No. 15/367,708, filed Dec. 2, 2016, Gao et al.
U.S. Appl. No. 15/423,702, filed Feb. 3, 2017, Gao et al.
U.S. Appl. No. 15/423,720, filed Feb. 3, 2017, Gao et al.
U.S. Appl. No. 15/516,582, filed Apr. 3, 2017, Esteves et al.
U.S. Appl. No. 15/516,585, filed Apr. 3, 2017, Esteves et al.
U.S. Appl. No. 15/567,847, filed Oct. 19, 2017, Esteves et al.
U.S. Appl. No. 15/568,650, filed Oct. 23, 2017, Gao et al.
U.S. Appl. No. 15/578,994, filed Dec. 1, 2017, Cataltepe.
U.S. Appl. No. 15/613,646, filed Jun. 5, 2017, Gao et al.
U.S. Appl. No. 15/747,801, filed Jan. 26, 2018, Fitzgerald et al.
Uniprot Submission; Accession No. A8IGP7; Nov. 13, 2013.
Uniprot Submission; Accession No. H3GK32; Feb. 6, 2013.
Uniprot Submission; Accession No. T2BRA8; Nov. 13, 2013.

(56) References Cited

OTHER PUBLICATIONS

Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Vaucheret et al., The action of Argonaute1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Watson et al., Intrathecal administration of AAV vectors for the treatment of lysosomal storage in the brains of MPS I mice. Gene Ther. Jun. 2006;13(11):917-25.
Wein et al., Efficient bypass of mutations in dysferlin deficient patient cells by antisense-induced exon skipping. Hum Mutat. Feb. 2010;31(2):136-42. doi: 10.1002/humu.21160.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Xia et al., Allele-specific RNAi selectively silences mutant SOD1 and achieves significant therapeutic benefit in vivo. Neurobiol Dis. Sep. 2006;23(3):578-86. Epub Jul. 20, 2006.
Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., MicroRNA regulated tissue specific transduction by rAAV vector. Molecular Therapy. May 2009;17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): S140. Abstract362.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.
Xu et al., Delivery of MDR1 small interfering RNA by self-complementary recombinant adeno-associated virus vector. Mol Ther. Apr. 2005;11(4):523-30.
Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.
Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.
Yu et al., let-7 regulates self renewal and tumorigenicity of breast cancer cells. Cell. Dec. 14, 2007;131(6):1109-23.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2):158-67.
Zu et al., RAN proteins and RNA foci from antisense transcripts in C9ORF72 Als and frontotemporal dementia. Proc Natl Acad Sci U S A. 2013;110(51):E4968-E4977. doi:10.1073/pnas.1315438110.
Kubodera et al., In vivo application of an RNAi strategy for the selective suppression of a mutant allele. Hum Gene Ther. Jan. 2011;22(1):27-34. doi: 10.1089/hum.2010.054. PMID: 20649474.
Lebedeva et al., Phosphorothioate Oligodeoxynucleotides as Inhibitors Of Gene Expression: Antisense and Non-Antisense Effects. In: Rabbani, L.E. (eds) Applications of Antisense Therapies to Restenosis. Perspectives in Antisense Science. 1999; 3:99-118. https://doi.org/10.1007/978-1-4615-5183-6_6.
Lino et al., Delivering CRISPR: a review of the challenges and approaches. Drug Deliv. Nov. 2018;25(1):1234-1257. doi: 10.1080/10717544.2018.1474964.
Third Party Submission under 37 CFR 1.290 for U.S. Appl. No. 16/611,581, filed May 7, 2021.

(56) References Cited

OTHER PUBLICATIONS

Partial European Search Report for Application No. EP 20183218.5, dated Nov. 10, 2020.

Extended European Search Report for Application No. EP 20183218.5, dated Mar. 31, 2021.

Extended European Search Report for Application No. EP 18797613.9, dated Dec. 8, 2020.

Third Party Submission under 37 CFR 1.290 for U.S. Appl. No. 16/611,581, filed May 2021.

Extended European Search Report for application No. EP 18859329.7, dated May 3, 2021.

Ciura et al., Loss of function of C9orf72 causes motor deficits in a zebrafish model of amyotrophic lateral sclerosis. Ann Neurol. Aug. 2013;74(2):180-7. doi: 10.1002/ana.23946.

Fernandes et al., Oligonucleotide-Based Therapy for FTD/ALS Caused by the C9orf72 Repeat Expansion: A Perspective. J Nucleic Acids. 2013;2013:208245(1-11). doi: 10.1155/2013/208245. Epub Nov. 17, 2013.

Lagier-Tourenne et al., Targeted degradation of sense and antisense C9orf72 RNA foci as therapy for ALS and frontotemporal degeneration. Proc Natl Acad Sci U S A. Nov. 19, 2013;110(47):E4530-9. doi: 10.1073/pnas.1318835110. Epub Oct. 29, 2013. Supporting Information, 17 pages.

Sareen et al., Targeting RNA foci in iPSC-derived motor neurons from ALS patients with a C9ORF72 repeat expansion. Sci Transl Med. Oct. 23, 2013;5(208):208ra149. doi: 10.1126/scitranslmed.3007529. Author Manuscript, 26 pages.

Stoica et al., Adeno-associated virus-delivered artificial microRNA extends survival and delays paralysis in an amyotrophic lateral sclerosis mouse model. Ann Neurol. Apr. 2016;79(4):687-700. doi: 10.1002/ana.24618. Epub Mar. 11, 2016. Author Manuscript. 24 pages.

Toro et al., 603. Artificial MicroRNAs Against Spliced Variants of the Gene C9ORF72, the Major Cause for Familial Amyotrophic Lateral Sclerosis. Mol Ther. May 2013;21(Supplement 1):S230-S231. doi: 10.1016/S1525-0016(16)34938-3.

Yamada et al., RNA interference (RNAi). Clinical Chemistry. Sep. 2005;34(3):216-223.

\* cited by examiner

FIG. 1A

METHODS OF TREATING AMYOTROPHIC LATERAL SCLEROSIS (ALS)

RELATED APPLICATIONS

This Application is a national stage filing under 35 U.S.C. § 371 of international PCT application, PCT/US2018/031880, filed May 9, 2018, entitled "METHODS OF TREATING AMYOTROPHIC LATERAL SCLEROSIS (ALS)," which claims the benefit under 35 U.S.C. 119(e) of the filing date of U.S. Provisional Application Ser. No. 62/503,909, filed May 9, 2017, the entire contents of each of which are incorporated herein by reference.

REFERENCE TO A SEQUENCE LISTING SUBMITTED AS A TEXT FILE VIA EFS-WEB

This Application contains a Sequence Listing which has been submitted in ASCII format via EFS-Web and is hereby incorporated by reference in its entirety. Said ASCII copy, created on Jan. 30, 2023, is named U012070092US01-SUBSEQ-LJG and is 6,728 bytes in size.

BACKGROUND

Amyotrophic Lateral Sclerosis (ALS) is a fatal neurodegenerative disease that is characterized by progressive loss of motor neurons, both in the brain (upper motor neurons) and the spinal cord (lower motor neurons). The average age of onset is in the late 50s-60s and the patients succumb to death in 3-5 years. The current estimated prevalence in the United States is 1 in 50,000 people. ALS is grouped into two categories depending on whether the disease is inherited or not; about 50-10% of cases are familial ALS and the remaining percentage falls under sporadic ALS. Mutations in more than 25 genes have been linked to ALS since the discovery of SOD1.

SUMMARY

Aspects of the disclosure relate to methods and compositions for treating ALS. Some aspects relate to a (GGGGCC)$_n$ repeat expansion in the non-coding region of the C9orf72 gene, which is a major cause for both familial (25-40%) and sporadic (7%) ALS. In some embodiments, the repeat expansion may lead to haploinsufficiency due to reduced C9orf72 transcript levels and/or reduced activity or function of C9orf72 gene products. In some embodiments, the repeat expansion may lead to nuclear RNA foci formation which leads to RNA and RNA binding protein sequestration. In some embodiments, the repeat expansion may lead to toxic dipeptide proteins produced through repeat-associated non ATG (RAN) translation. The disclosure is based, in part, on gene editing molecules (e.g., RNAs, such as guide RNAs (gRNAs), trans-activating crRNA (tracrRNA), etc., proteins, such as CRISPR/Cas proteins, etc., and complexes of RNAs and CRISPR/Cas proteins) that direct cleavage, excision, or degradation of (GGGCC)$_n$ repeat expansions in a C9orf72 gene. Accordingly, some aspects of the disclosure relate to methods for treating C9FTD/ALS that involve editing (e.g., physically erasing) the repeat expansions from the C9ORF72 genomic locus to restore the gene to a normal or healthy state.

In some embodiments, methods provided herein involve use of CRISPR/Cas9-guided genome editing or related systems. In some embodiments, CRISPR/Cas9 functions as a nuclease that can make double-strand breaks in genomic DNA. In some embodiments, CRISPR/Cas9 is guided to a target sequence by an associated guide RNA, e.g., with ~20 nucleotides of complementarity to the target sequence. In some embodiments, CRISPR/Cas9 related methods provided herein involve delivery of the Cas9 enzyme with a guide RNA via one or more AAV vectors.

In some embodiments, methods provided herein alleviate the cause of ALS in patients with C9orf72 specific mutations. Further aspects of the disclosure relate to methods for targeting (e.g., using gene editing systems (e.g., CRISPR/Cas9)) the repeat expansion in the intronic region without affecting any of the exons. In some embodiments, guide RNAs have been developed that are capable of directing the removal of the repeat region using CRISPR Cas9 system. In some embodiments, the RNA guides are packaged into rAAV vectors (e.g., rAAV9 vectors) for in vivo delivery. In some embodiments, gene editing occurs in primary neurons in culture. In some embodiments, gene editing occurs in animals in vivo, e.g., in mice through tail vein injections.

Accordingly, in some aspects, the disclosure provides an isolated nucleic acid comprising the sequence set forth in any one of SEQ ID NOs: 1 to 6, or a sequence complementary to any one of them.

In some aspects, the disclosure provides an isolated nucleic acid comprising a nucleic acid sequence encoding a guide RNA (gRNA) having the sequence set forth in any one of SEQ ID NOs: 1-6, or a sequence complementary to any one of them.

In some embodiments, an isolated nucleic acid sequence is flanked by adeno-associated virus (AAV) inverted terminal repeats (ITRs). In some embodiments, AAV ITRs are AAV2 ITRs, AAV3 ITRs, AAV4 ITRs, AAV5 ITRs, AAV6 ITRs, AAV7 ITRs, AAV8 ITRs, or AAV9 ITRs.

In some aspects, the disclosure provides an isolated nucleic acid comprising a transgene encoding two or more guide RNAs (gRNAs) that specifically hybridize to a target nucleic acid sequence flanking opposite sides of a $G_4C_2$ repeat of a C9ORF72 gene, flanked by adeno-associated virus (AAV) inverted terminal repeats (ITRs).

In some embodiments, two or more gRNAs each comprise or consist of the sequence set forth in any one of SEQ ID NOs: 1-4, or a sequence complementary to any one of them.

In some embodiments, a transgene encodes a first gRNA having the sequence set forth in SEQ ID NO: 1 and a second gRNA having the sequence set forth in SEQ ID NO: 3. In some embodiments, a transgene encodes a first gRNA having the sequence set forth in SEQ ID NO: 2 and a second gRNA having the sequence set forth in SEQ ID NO: 3.

In some embodiments, a transgene comprises a promoter. In some embodiments, a promoter is a CB promoter.

In some aspects, the disclosure provides a recombinant adeno-associated virus (rAAV) comprising an isolated nucleic acid as described by the disclosure; and at least one AAV capsid protein.

In some embodiments, a capsid protein is of a serotype selected from AAV1, AAV2, AAV3, AAV4, AAV5, AAV6, AAV7, AAV8, AAV9, or a variant of any of the foregoing. In some embodiments, a capsid protein is an AAV9 capsid protein.

In some aspects, the disclosure provides a composition comprising an rAAV as described by the disclosure, and a recombinant gene editing protein. In some embodiments, a recombinant gene editing protein is encoded by an rAAV vector. In some embodiments, a recombinant gene editing protein is a CRISPR/Cas protein, optionally a Cas9 protein.

In some aspects, the disclosure provides a mammalian cell expressing: two or more guide RNAs (gRNAs) that specifically hybridize to a target nucleic acid sequence flanking opposite sides of a $G_4C_2$ repeat of a C9ORF72 gene; and a recombinant gene editing protein that interacts with the two or more gRNAs.

In some embodiments, a recombinant gene editing protein is a CRISPR/Cas protein. In some embodiments, a recombinant gene editing protein is a Cas protein selected from Cas9, Cas6, and Cpf1. In some embodiments, a recombinant gene editing protein is Cas9.

In some embodiments, each of the gRNAs comprises the sequence set forth in any one of SEQ ID NOs: 1 to 4, or a sequence complementary to any one of them.

In some embodiments, a mammalian cell expresses 2, 3, or 4 gRNAs that each specifically hybridizes to a target nucleic acid sequence flanking opposite sides of a $G_4C_2$ repeat of a C9ORF72 gene.

In some embodiments, a mammalian cell expresses a first gRNA having the sequence set forth in SEQ ID NO: 1 and a second gRNA having the sequence set forth in SEQ ID NO: 3.

In some embodiments, a mammalian cell expresses a first gRNA having the sequence set forth in SEQ ID NO: 2 and a second gRNA having the sequence set forth in SEQ ID NO: 3.

In some embodiments, a mammalian cell further expresses a trans-activating crRNA (tracrRNA).

In some embodiments, a target nucleic acid sequence is positioned in a non-protein-coding region between Exon 1b and Exon 2 of the C9ORF72 gene, or is positioned in a non-protein-coding region between Exon 2 and Exon 3 of the C9ORF72 gene.

In some aspects, the disclosure provides a method comprising delivering to a cell: a recombinant gene editing protein; and two or more guide RNAs (gRNAs) that specifically hybridize to target nucleic acid sequences flanking opposite sides of a $G_4C_2$ repeat of a C9ORF72 gene.

In some embodiments, delivery of a recombinant gene editing protein and gRNAs to a cell results in removal of the $G_4C2$ repeat from at least one allele of the C9ORF72 gene in the cell.

In some embodiments, a recombinant gene editing protein and/or gRNAs are delivered to a cell using a recombinant AAV vector comprising a nucleic acid engineered to express the protein or gRNAs in the cell.

In some embodiments, a cell is in vivo. In some embodiments, a cell is a primary neuron.

In some embodiments, a recombinant AAV vector comprises an AAV9 capsid protein or variant thereof.

In some embodiments, a gRNA comprises a sequence selected from SEQ ID NO: 1-4 or a sequence complementary to any one of them.

In some embodiments, the disclosure provides a mammalian cell expressing a guide RNA (gRNA) that specifically hybridizes to an exonic region of a C9ORF72 gene; and a recombinant gene editing protein that interacts with the gRNA.

In some embodiments, a recombinant gene editing protein is a CRISPR/Cas protein. In some embodiments, a recombinant gene editing protein is a Cas protein selected from Cas9, Cas6, and Cpf1. In some embodiments, a recombinant gene editing protein is Cas9.

In some embodiments, a gRNA comprises the sequence set forth in SEQ ID NO: 5 or 6, or a sequence complementary to either one of them.

In some embodiments, a mammalian cell further comprises a trans-activating crRNA (tracrRNA).

In some embodiments, interaction of a gRNA and a recombinant gene editing protein results in formation of a complex, and binding of the complex to the C9ORF72 gene results in non-sense mediated decay of the C9ORF72 gene.

In some aspects, the disclosure provides a method of reducing RNA foci and/or dipeptide formation in a cell, the method comprising expressing in the cell a recombinant gene editing complex comprising a guide RNA (gRNA) that specifically hybridizes to an exonic region of a C9ORF72 gene and a recombinant gene editing protein that interacts with the gRNA, wherein delivery of the recombinant gene editing complex to the cell results in insertions or deletions in the C9ORF72 gene that lead to non-sense mediated decay of C9orf72 transcripts transcribed from the gene.

In some embodiments, a recombinant gene editing protein and/or gRNA(s) of a complex are expressed in a cell using a recombinant AAV vector comprising a nucleic acid engineered to express the protein or gRNAs in the cell.

In some embodiments, a cell is in vivo. In some embodiments, a cell is a primary neuron.

In some embodiments, a recombinant AAV vector comprises an AAV9 capsid protein or variant thereof.

In some embodiments, a gRNA comprises a sequence selected from SEQ ID NO: 5 or 6, or a sequence complementary to either one of them.

In some embodiments, the disclosure provides a method comprising delivering to a cell: a guide RNA (gRNA) that specifically hybridizes to one or more exonic regions of a C9ORF72 gene; and a recombinant gene editing protein that interacts with the gRNA.

In some embodiments, the method further comprises delivering to the cell two guide RNAs that specifically hybridize to different positions within the same exon of a C9ORF72 gene.

In some embodiments, an exonic region is within exon 3 of the C9ORF72 gene.

In some embodiments, a recombinant gene editing protein and/or gRNA(s) is/are delivered to a cell using a recombinant AAV vector comprising a nucleic acid engineered to express the protein or gRNAs in the cell.

In some embodiments, delivery of a recombinant gene editing protein and gRNAs to a cell results in insertions or deletions in the C9ORF72 gene that lead to non-sense mediated decay of C9orf72 transcripts transcribed from the gene.

In some embodiments, a gRNA comprises a sequence selected from SEQ ID NO: 5 or 6, or a sequence complementary to either one of them.

In some embodiments, a recombinant gene editing protein is a Crisper/Cas9 protein.

In some aspects, the disclosure provides a recombinant gene editing complex configured to remove all or a portion of the $G_4C_2$ repeat from at least one allele of a C9ORF72 gene in a cell or to induce an insertion or deletion within an exonic region of the C9ORF72 gene in the cell that results in non-sense mediated decay of C9orf72 transcripts transcribed from the gene.

In some embodiments, the disclosure provides a method comprising delivering to a cell: one or more guide RNAs (gRNAs) that specifically hybridize to target nucleic acid sequences flanking opposite sides of a G4C2 repeat of a C9ORF72 gene; or one or more guide RNAs (gRNAs) that specifically hybridize to one or more exonic regions of a C9ORF72 gene.

In some embodiments, a cell expresses a recombinant gene editing protein that binds to one or more guide RNAs (gRNAs).

BRIEF DESCRIPTION OF DRAWINGS

Figure 1A:
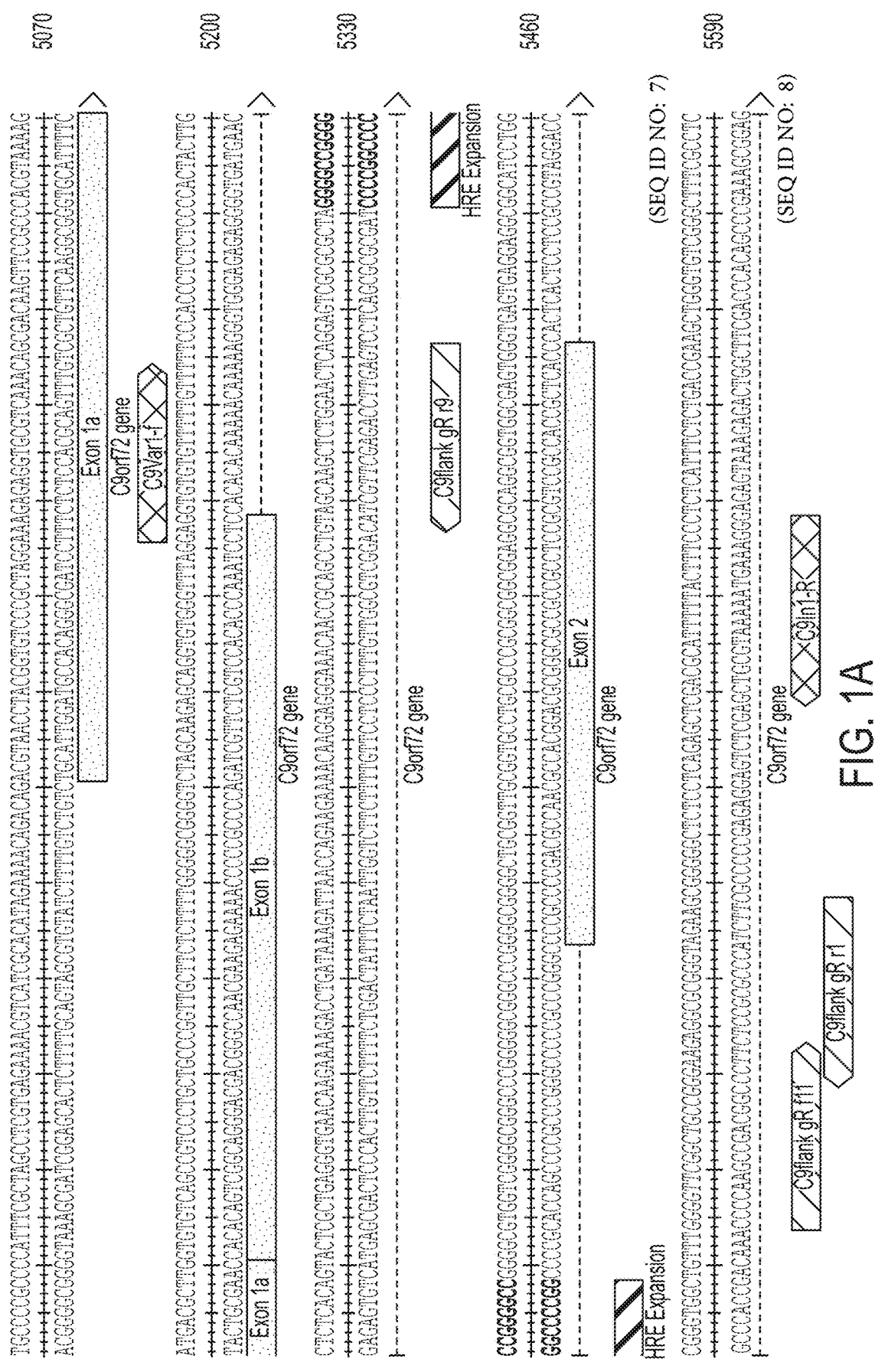

FIGS. 1A to 1C show guide RNAs described in Example 1. FIG. 1A shows the human C9orf72 (NG_031977.1) gene sequence surrounding the $G_4C_2$ expansion repeat. RNAs r9 (also referred to as "gr-r9" or "gRNA 2"), f11 (also referred to as "gr-f11" or "gRNA 3"), and r1=(also referred to as "gr-r1" or "gRNA 4"); PCR primers C9Var1-f and C9In1-R. FIG. 1B shows a schematic representation of the C9 region containing the $(GGGCC)_n$ expansion. Relative positioning of the repeat expansion of $G_4C2$, non-coding Exon 2, RNA guides gr-r9, gr-r1, and gr-f11, editing primers C9Var1-f and C9Ind1-R, no editing forward primer NoE-F1, and the repeat primed PCR primer RP-PCR-R is shown. FIG. 1C shows design and testing of gRNAs in HEK 293 cells. Since the repeat expansion is close to exon 2, the only efficient guide on the 3' end would also span exon 2 (which is un translated). In HEK 293 cells, there is only 3 "GGGGCC" repeats-successful editing will reduce the size of the PCR product using the two indicated primers from 520 bp to around 315 bp. Vectors containing gRNA combination 2-3 and 2-4 were the most efficient and were subsequently packaged in AAV9 capsid protein.

FIG. 2A shows agarose electrophoresis of PCR products amplified by C9Var1-f and C9In1-R primers. Unedited PCR product size is 523 bp; edited PCR product size for gRNA 1 & 4(f1+r1) and gRNA 1 & 3 (f1+f11) is ~250 bp; edited PCR product by gRNA 2 & 3 (r9+f11) and gRNA 2 & 4 (r9+r1) is ~320 bp (+/− several base pairs with indels). FIG. 2B shows an alignment of the sequence of the PCR products gel extracted from FIG. 2A (indicated with arrows).

FIG. 6A shows human C9orf72 gene sequence of exon 3. The locations of non-sense mediated decay (NMD) guide RNA 1r and 2f and the location and sequence of PCR indel analysis primers C9NMD Indel F1 and R1 are indicated. FIG. 6B shows agarose gel electrophoresis of PCR products amplified by C9NMD-Indel F1 and R1 PCR primers. HEK293T cells were transfected with LV-SpCas9 (Control) or LV-NMDgR-SpCas9 plasmid (2 µg) in triplicate. FIG. 6C shows digital droplet PCR (ddPCR) analysis of C9orf72 RNA level in cells from FIG. 6B. All variants of C9orf72 are detected with this particular probe-primer set. (Input RNA—10 ng per sample) * p<0.001.

FIG. 8A shows fluorescence micrographs of neurons infected with PBS, AAV9-ssGFP, AAV9-ROSA-tRFP, AAV9-gRNA 2 & 3, or AAV9-gRNA 2-4. FIG. 8B shows PCR amplification of edited DNA from cultured neurons amplified with C9Var1-F & NoER2 primers, as well as amplification of non-edited DNA using primers NoE-F1 and NoER2. Intensity of the band amplified by the second set of primers was significantly less in the edited samples.

FIG. 10A shows fluorescence of neurons infected with Cas9, AAV9-ssGFP+Cas9, AAV9-ROSA-tRFP+Cas9, AAV9-gRNA 2-3+Cas9, or AAV9-gRNA 2-4+Cas9. FIG. 10B shows PCR amplification of edited DNA from cultured neurons amplified with C9Var1-F & NoER2. Amplification bands occur only in edited cells (e.g., cells treated with AAV9-gRNA 2-3+Cas9, or AAV9-gRNA 2-4+Cas9).

FIG. 14A shows the injection site and the brain slice used for tissue isolation. FIG. 14B shows that injection of PBS+Cas9, ROSA-tRFP+Cas9, gRNA 2 & 3+Cas9, gRNA 2 & 4+Cas9 promotes gene editing in Baloh C9 mice and BAC111 C9/Cas9 mice.

DETAILED DESCRIPTION

Figure 1B:
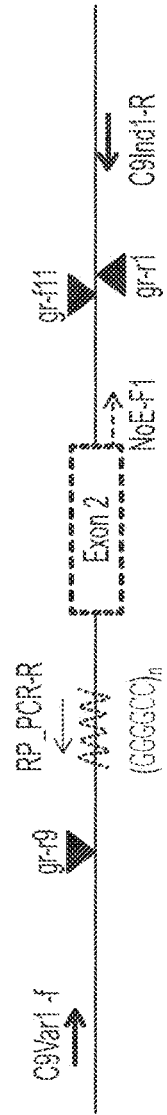

Through genetic linkage analysis of familial ALS patients, several genes have been identified to be risk factors for ALS. In the first intron of chromosome 9 open reading frame 72 (C9orf72), a large repeat expansion consisting of GGGGCC hexanucleotide has been identified in families of familial ALS patients. These microsatellite expansions can be transcribed in a bidirectional manner, producing both sense and antisense transcripts. The RNA transcripts accumulate in the nucleus of affected regions in the brain as RNA foci; moreover, repeat-associated non-ATG (RAN) translation of the transcripts leads to generation of dipeptide aggregates in the neuronal cytoplasm within the affected region. There is evidence indicating dipeptides and RNA foci may be toxic and may disrupt nucleocytoplasmic transport, autophagy, and immune response.

Provided herein are methods and related compositions useful for reducing or removing (e.g., completely removing) GGGGCC (e.g., $G_4C_2$) repeat expansions. In some embodiments, methods provided herein reduce the accumulation of RNA foci and dipeptide aggregates in the nucleus and cytoplasm, respectively. To accomplish this, a gene editing approach involving CRISPR/Cas9 nuclease and guide RNAs targeted at different regions of C9orf72 gene were used in some embodiments. In some embodiments, strategies are outlined to excise the GGGGCC repeat in both in vitro and in vivo mice models.

Gene Editing Molecules

In some aspects, the disclosure provides a recombinant gene editing complex comprising: a recombinant gene editing protein; and, a nucleic acid encoding a guide RNA (gRNA) that specifically hybridizes to a target nucleic acid sequence within the C9ORF72 locus that are useful for excising all or a portion of a GGGGCC repeat expansion.

As used herein, "gene editing complex" refers to a biologically active molecule (e.g., a protein, one or more proteins, a nucleic acid, one or more nucleic acids, or any combination of the foregoing) configured for adding, disrupting or changing genomic sequences (e.g., a gene sequence), for example by causing one or more double stranded breaks (DSBs) in a target DNA. Examples of gene editing complexes include but are not limited to Transcription Activator-like Effector Nucleases (TALENs), Zinc Finger Nucleases (ZFNs), engineered meganuclease re-engineered homing endonucleases, the CRISPR/Cas system, and meganucleases (e.g., Meganuclease I-SceI). In some embodiments, a gene editing complex comprises proteins or molecules (e.g., recombinant gene editing proteins) related to the CRISPR/Cas system, including but not limited to Cas9, Cas6, Cpf1, CRISPR RNA (crRNA), trans-activating crRNA (tracrRNA), and variants thereof.

In some embodiments, a recombinant gene editing protein is a nuclease. As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), meganucleases (e.g., engineered meganucleases) and CRISPR-associated proteins (Cas nucleases). In some embodiments, the nuclease is a ZFN. In some embodiments, the ZFN comprises a FokI cleavage domain. In some embodiments, the ZFN comprises $Cys_2His_2$ fold group. In some embodiments, the nuclease is a TALEN. In some embodiments, the TALEN comprises a FokI cleavage domain. In some embodiments, the nuclease is a meganuclease. Examples of meganucleases include but are not limited to I-SceI, I-CreI, I-DmoI, and combinations thereof (e.g., E-DreI, DmoCre).

The term "CRISPR" refers to "clustered regularly interspaced short palindromic repeats", which are DNA loci containing short repetitions of base sequences. CRISPR loci form a portion of a prokaryotic adaptive immune system that confers resistance to foreign genetic material. Each CRISPR loci is flanked by short segments of "spacer DNA", which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease). Examples of CRISPR nucleases include, but are not limited to Cas9, dCas9, Cas6, Cpf1, and variants thereof. In some embodiments, the nuclease is Cas9. In some embodiments, the Cas9 is derived from the bacteria *Streptococcus pyogenes* (e.g., SpCas9) or *Staphylococcus aureus* (e.g., SaCas9). In some embodiments, a Cas protein or variant thereof does not exceed the packaging capacity of a viral vector, such as a lentiviral vector or an adeno-associated virus (AAV) vector, for example as described by Ran et al. (2015) *Nature*. 520(7546); 186-91. For example, in some embodiments, a nucleic acid encoding a Cas protein is less than about 4.6 kb in length.

For the purpose of genome editing, the CRISPR system can be modified to combine the tracrRNA and crRNA in to a single guide RNA (sgRNA) or just (gRNA). As used herein, the terms "guide RNA", "gRNA", and "sgRNA" refer to a polynucleotide sequence that is complementary to a target sequence in a cell and associates with a Cas nuclease, thereby directing the Cas nuclease to the target sequence. In some embodiments, a gRNA (e.g., sgRNA) ranges between 1 and 30 nucleotides in length. In some embodiments, a gRNA (e.g., sgRNA) ranges between 5 and 25 nucleotides in length. In some embodiments, a gRNA (e.g., sgRNA) ranges between 10 and 22 nucleotides in length. In some embodiments, a gRNA (e.g., sgRNA) ranges between 14 and 24 nucleotides in length. In some embodiments, a Cas protein and a guide RNA (e.g., sgRNA) are expressed from the same vector. In some embodiments, a Cas protein and a guide RNA (e.g., sgRNA) are expressed from separate vectors (e.g., two or more vectors).

Typically, a guide RNA (e.g., a gRNA or sgRNA) hybridizes (e.g., binds specifically to, for example by Watson-Crick base pairing) to a target sequence and thus directs the CRISPR/Cas protein or simple protein to the target sequence. In some embodiments, a guide RNA hybridizes to (e.g., targets) a nucleic acid sequence, e.g., within a C9ORF72 locus. In some embodiments, a guide RNA hybridizes to a target sequence on the sense strand (e.g., 5'-3' strand) of a gene. In some embodiments, a guide RNA hybridizes to a target sequence on the antisense strand (e.g., 3'-5' strand) of a gene.

In some aspects, the disclosure relates to guide RNAs (gRNAs) that specifically hybridize to a target nucleic acid sequence flanking opposite sides of a $G_4C_2$ repeat of a C9ORF72 gene. As used herein "flanking opposite sides of a $G_4C_2$ repeat" refers to a first portion of a target nucleic acid sequence that is upstream (e.g., 5') with respect to a $G_4C_2$ repeat and a second portion of a target nucleic acid sequence that is downstream (e.g., 3') with respect to a $G_4C_2$ repeat (and also the first portion). For example, gRNA-R9 and gRNA-R1 represent a pair of gRNAs that specifically hybridize to a target nucleic acid sequence flanking opposite sides of a $G_4C_2$ repeat, as shown in FIG. 1A.

In some embodiments, a sequence that flanks a $G_4C_2$ repeat is positioned between 1 nucleotide and 1000 nucleotides (e.g., any integer between 1 and 1000) upstream (e.g., 5') with respect to a $G_4C_2$ repeat (e.g., the first GGGGCC unit of the repeat). In some embodiments, a sequence that flanks a $G_4C_2$ repeat is positioned between 10 nucleotides and 800 nucleotides upstream (e.g., 5') with respect to a $G_4C_2$ repeat. In some embodiments, a sequence that flanks a $G_4C_2$ repeat is positioned between 200 nucleotides and 700 nucleotides upstream (e.g., 5') with respect to a $G_4C_2$ repeat. In some embodiments, a sequence that flanks a $G_4C_2$ repeat is positioned between more than 1000 nucleotides (e.g., 1500, 2000, 2500, 5000, or more) upstream (e.g., 5') with respect to a $G_4C_2$ repeat.

In some embodiments, a sequence that flanks a $G_4C_2$ repeat is positioned between 1 nucleotide and 1000 nucleotides (e.g., any integer between 1 and 1000) downstream (e.g., 3') with respect to a $G_4C_2$ repeat (e.g., the last GGGGCC unit of the repeat). In some embodiments, a sequence that flanks a $G_4C_2$ repeat is positioned between 10 nucleotides and 800 nucleotides downstream (e.g., 3') with respect to a $G_4C_2$ repeat. In some embodiments, a sequence that flanks a $G_4C_2$ repeat is positioned between 200 nucleotides and 700 nucleotides downstream (e.g., 3') with respect to a $G_4C_2$ repeat. In some embodiments, a sequence that flanks a $G_4C_2$ repeat is positioned between more than 1000 nucleotides (e.g., 1500, 2000, 2500, 5000, or more) downstream (e.g., 3') with respect to a $G_4C_2$ repeat.

Methods of Treatment

In some aspects, the disclosure provides methods for treating a subject having ALS or at risk of having ALS. A subject can be a human, non-human primate, rat, mouse, cat, dog, or other mammal.

As used herein, the terms "treatment", "treating", and "therapy" refer to therapeutic treatment and prophylactic or preventative manipulations. The terms further include ameliorating existing symptoms, preventing additional symptoms, ameliorating or preventing the underlying causes of symptoms, preventing or reversing causes of symptoms, for example, symptoms associated with ALS. Thus, the terms denote that a beneficial result has been conferred on a subject having ALS, or with the potential to develop such a disorder. Furthermore, treatment may include the application or administration of an agent (e.g., therapeutic agent or a therapeutic composition) to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease.

Therapeutic agents or therapeutic compositions may include a compound, vector, etc. in a pharmaceutically acceptable form that prevents and/or reduces the symptoms of a particular disease (e.g., ALS). For example a therapeutic composition may be a pharmaceutical composition that prevents and/or reduces the symptoms of ALS. In some embodiments, the disclosure provides a composition (e.g., a therapeutic composition) comprising one or more components of, or encoding, a gene editing complex as described by the disclosure, e.g., a vector as described by the disclosure. In some embodiments, the composition further comprises a pharmaceutically acceptable excipient. It is contemplated that the therapeutic composition of the present invention will be provided in any suitable form. The form of the therapeutic composition will depend on a number of factors, including the mode of administration as described herein. The therapeutic composition may contain diluents, adjuvants and excipients, among other ingredients as described herein.

Pharmaceutical Compositions

In some aspects, the disclosure relates to pharmaceutical compositions comprising a gene editing complex. In some embodiments, the composition comprises gene editing complex and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described herein. The active ingredients may be admixed or compounded with any conventional, pharmaceutically acceptable carrier or excipient. The compositions may be sterile.

Typically, pharmaceutical compositions are formulated for delivering an effective amount of an agent (e.g., gene editing complex). In general, an "effective amount" of an active agent refers to an amount sufficient to elicit the desired biological response. An effective amount of an agent may vary depending on such factors as the desired biological endpoint, the pharmacokinetics of the compound, the disease being treated (e.g., ALS), the mode of administration, and the patient.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. It will be understood by those skilled in the art that any mode of administration, vehicle or carrier conventionally employed and which is inert with respect to the active agent may be utilized for preparing and administering the pharmaceutical compositions of the present disclosure.

An effective amount, also referred to as a therapeutically effective amount, of a compound (for example, a gene editing complex or vector as described by the disclosure) is an amount sufficient to ameliorate at least one adverse effect associated with a condition (e.g., ALS). In the case of viral vectors, an amount of active agent can be included in each dosage form to provide between about $10^{10}$, $10^{11}$, $10^{12}$, $10^{13}$, $10^{14}$, or $10^{15}$ genome copies per subject. One of ordinary skill in the art would be able to determine empirically an appropriate therapeutically effective amount.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above.

The compositions may conveniently be presented in unit dosage form. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. In some embodiments, liquid dose units are vials or ampoules. In some embodiments, solid dose units are tablets, capsules and suppositories.

Modes of Administration

In some embodiments, a therapeutically effective amount of a gene editing complex or vector as described by the disclosure is delivered to a target tissue or a target cell. The pharmaceutical compositions containing gene editing complex or vector, and/or other compounds can be administered by any suitable route for administering medications. A variety of administration routes are available, including parenterally, intravenously, intrathecally, intracranially, intradermally, intramuscularly or subcutaneously, or transdermally. The methods of this disclosure, generally speaking, may be practiced using any mode of administration that is medically acceptable, meaning any mode that produces therapeutic effect without causing clinically unacceptable adverse effects. Various modes of administration are discussed herein. For use in therapy, an effective amount of the gene editing complex or vector, and/or other therapeutic agent can be administered to a subject by any mode that delivers the agent to the desired tissue, e.g., systemic, intramuscular, etc. In some embodiments, the gene editing complex or vector as described by the disclosure is administered to a subject via intramuscular (IM) injection or intravenously.

In some embodiments, a gene editing complex (e.g., a nucleic acid encoding one or more components of a gene editing complex) can be delivered to the cells via an expression vector engineered to express the gene editing complex. An expression vector is one into which a desired sequence may be inserted, e.g., by restriction and ligation, such that it is operably joined to regulatory sequences and may be expressed as an RNA transcript. An expression vector typically contains an insert that is a coding sequence for a protein (e.g., gene editing protein, such as a CRISPR/Cas protein) or for a polynucleotide, such as guide RNA (gRNA, sgRNA, etc.). Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays or fluorescent proteins, etc.

As used herein, a coding sequence (e.g., protein coding sequence, miRNA sequence, shRNA sequence) and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence may encode an functional RNA.

The precise nature of the regulatory sequences needed for gene expression may vary between species or cell types, but shall in general include, as necessary, 5' non-transcribed and 5' non-translated sequences involved with the initiation of transcription and translation, respectively, such as a TATA box, capping sequence, CAAT sequence, and the like. Such 5' non-transcribed regulatory sequences will include a promoter region that includes a promoter sequence for transcriptional control of the operably joined gene. However, in some embodiments, a vector does not include a promoter sequence. Regulatory sequences may also include enhancer sequences, upstream activator sequences, internal ribosomal entry sites (IRES), and/or self-processing peptide sequences (e.g., 2A peptide), as desired. The vectors of the disclosure may optionally include 5' leader or signal sequences.

In some embodiments, a virus vector for delivering a nucleic acid molecule is selected from the group consisting of adenoviruses, adeno-associated viruses, lentiviral vectors, etc. In some embodiments, the viral vector is a recombinant adeno-associated virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. The adeno-associated virus can also function in an extrachromosomal fashion.

In some embodiments, a recombinant AAV vector (rAAV) comprises, at a minimum, a transgene coding sequence (e.g., a nucleic acid sequence encoding a gene editing protein, such as a Cas protein, or a gRNA) and its associated regulatory sequence flanked by two AAV inverted terminal repeat (ITR) sequences. Examples of regulatory sequences include promoters (e.g., constitutive promoters, inducible promoters, tissue-specific promoters), enhancer sequences, etc. In some embodiments, the ITR sequences are AAV1, AAV2, AAV5, AAV6, AAV7, AAV8, or AAV9 ITR sequences, or variants thereof.

In some embodiments, an rAAV vector comprising a nucleic acid encoding all or part of a gene editing complex (e.g., a nucleic acid sequence encoding a gene editing protein, a gRNA, or both) is packaged into a recombinant AAV (rAAV). Typically, an AAV vector is packaged into viral particles comprising one or more AAV capsid proteins. In some embodiments, the AAV capsid is an important element in determining these tissue-specific targeting capabilities. Thus, an rAAV having a capsid appropriate for the tissue being targeted can be selected. In some embodiments, the capsid protein has a serotype selected from AAV2, AAV3, AAV5, AAV6, AAV6.2, AAV7, AAV8, AAV9, AAVrh.8, AAVrh.10, AAVrh.39, and AAVrh.43 or suitable variants of any one of them. In some embodiments, the rAAV comprises a capsid protein that targets neuronal cells.

In some embodiments, other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (e.g., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, New Jersey (1991). In some embodiments, gene editing complex (e.g., a nucleic acid sequence encoding a gene editing protein, a gRNA, or both) is delivered to a cell (e.g. a cell of a subject) by a lentiviral vector.

Various techniques may be employed for introducing nucleic acid molecules of the disclosure into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FectoFly™ transfection reagents for insect cells by Polyplus Transfection, Polyethylenimine "Max" by Polysciences, Inc., Unique, Non-Viral Transfection Tool by Cosmo Bio Co., Ltd., Lipofectamine™ LTX Transfection Reagent by Invitrogen, SatisFection™ Transfection Reagent by Stratagene, Lipofectamine™ Transfection Reagent by Invitrogen, FuGENE® HD Transfection Reagent by Roche Applied Science, GMP compliant in vivo-jetPEI™ transfection reagent by Polyplus Transfection, and Insect GeneJuice® Transfection Reagent by Novagen.

EXAMPLES

Example 1: Excision of $G_4C_2$ Expansion

Strategy Design and Testing in HEK Cells.

Figure 1C:
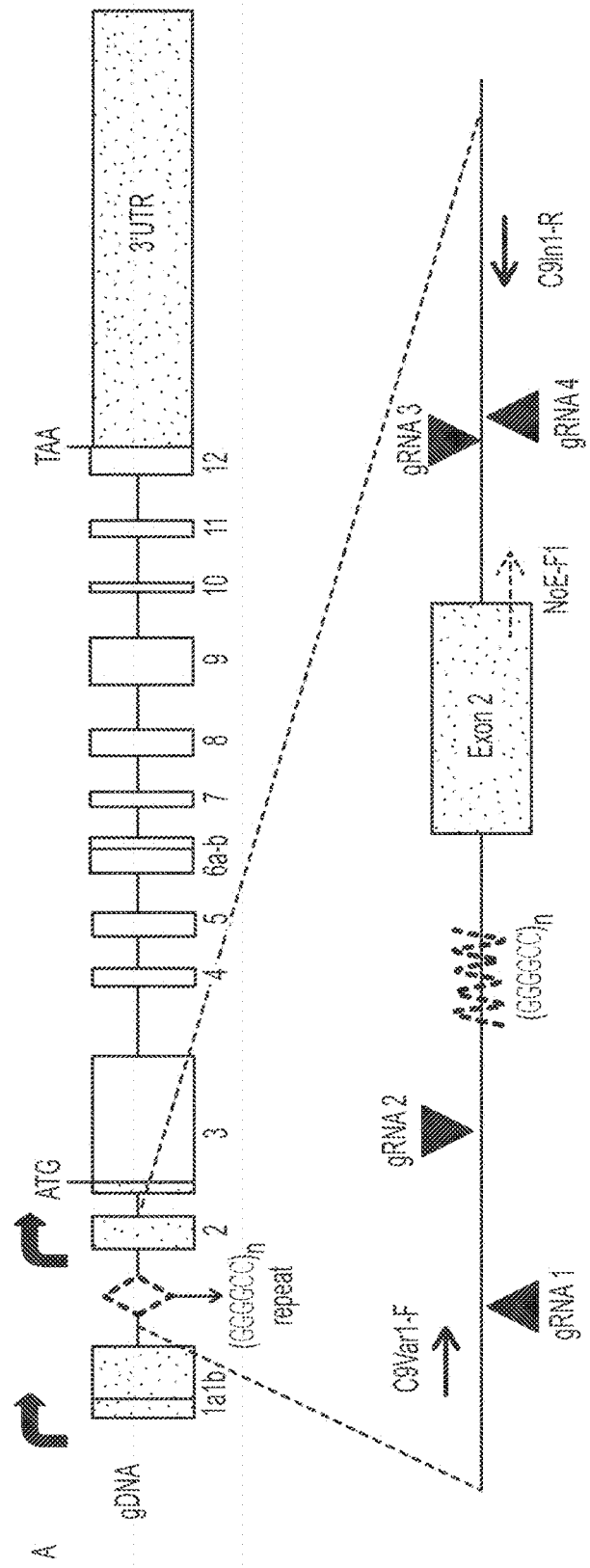

This example describes removal of the $G_4C_2$ expansion repeat in C9Orf72 using a CRISPR/Cas9 system. Several guide RNAs targeting the flanking regions of the $G_4C_2$ expansion were designed. The $G_4C_2$ expansion and guide RNAs are shown in FIG. 1A. Guides determined to be successful in achieving significant editing, as described herein, are shown. In order to test gene editing events, two primers, C9Var1-F and C9In1-R, that span the repeat expansion and the guides were designed (FIGS. 1A-1C). These primers can amplify through few repeats, but will generally not amplify through the 45-60 repeats present in the BAC436 mouse model. In order to detect no editing in the BAC436 model, a NoE-F1 primer that can in conjugation with C9In1-R-amplify ~120 bp band in unedited DNA, was designed (FIGS. 1B-1C). Another primer that recognizes the GGGGCC sequence within the repeat was designed (FIGS. 1B-1C). This primer was used for the repeat primed PCR (RP-PCR) described herein.

Figure 2A:
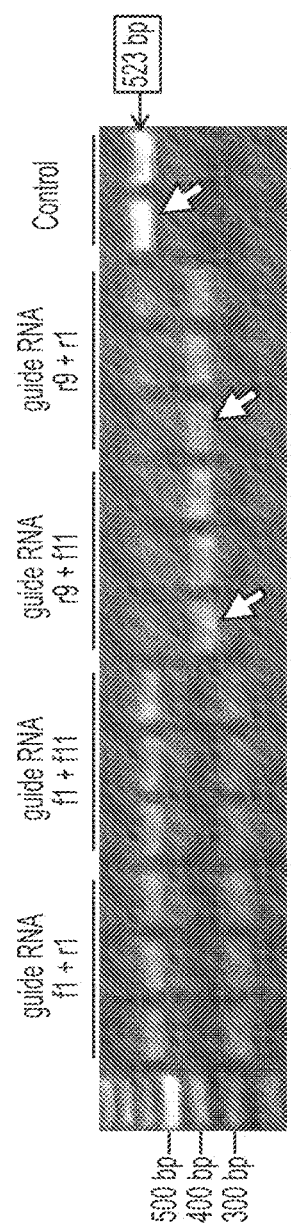
FIGS. 2A to 2B show data on Cas9-mediated C9orf72 $G_4C_2$ editing.

Four different guide RNA constructs, two on the 5' end of the repeat expansion (f1, also referred to as "gRNA1" & r9, also referred to as "gRNA 2") and two on the 3' end (r1, also referred to as "gRNA 4"& f11, also referred to as "gRNA 3") (Table 1), were generated. Then, plasmids expressing two of each guides as follows were generated: gRNA f1-r1, gRNA f1-f11, gRNA r9-f11, gRNA r9-r1. Each of these plasmids was co-transfected into HEK293T cells with another plasmid expressing S. pyogenes Cas9. DNA was extracted from these HEK 293T cells and a PCR was performed using C9Var1-F and C9In1-R. The products were run on an agarose gel (FIG. 2A). In case no editing occurs, these primers will amplify a 523 bp band. In case editing occurs, gRNA f1-r1 and f1-f11 will produce a ~250 bp band while r9-f11 and r9-r1 will produce a ~320 bp band.

TABLE 1

| Guide RNAs generated for "Excision of $G_4C_2$ expansion." | | |
|---|---|---|
| guide RNA name | guide RNA sequence | SEQ ID NO: |
| gRNA-f11 | GGGGUUCGGCUGCCGGGAAG | 1 |
| gRNA-r1 | GGAAGAGGCGCGGGUAGAAG | 2 |
| gRNA-r9 | GUAGCAAGCUCUGGAACUCA | 3 |
| gRNA-f1 | UGCUCUCACAGUACUCGCUG | 4 |

Figure 2B:
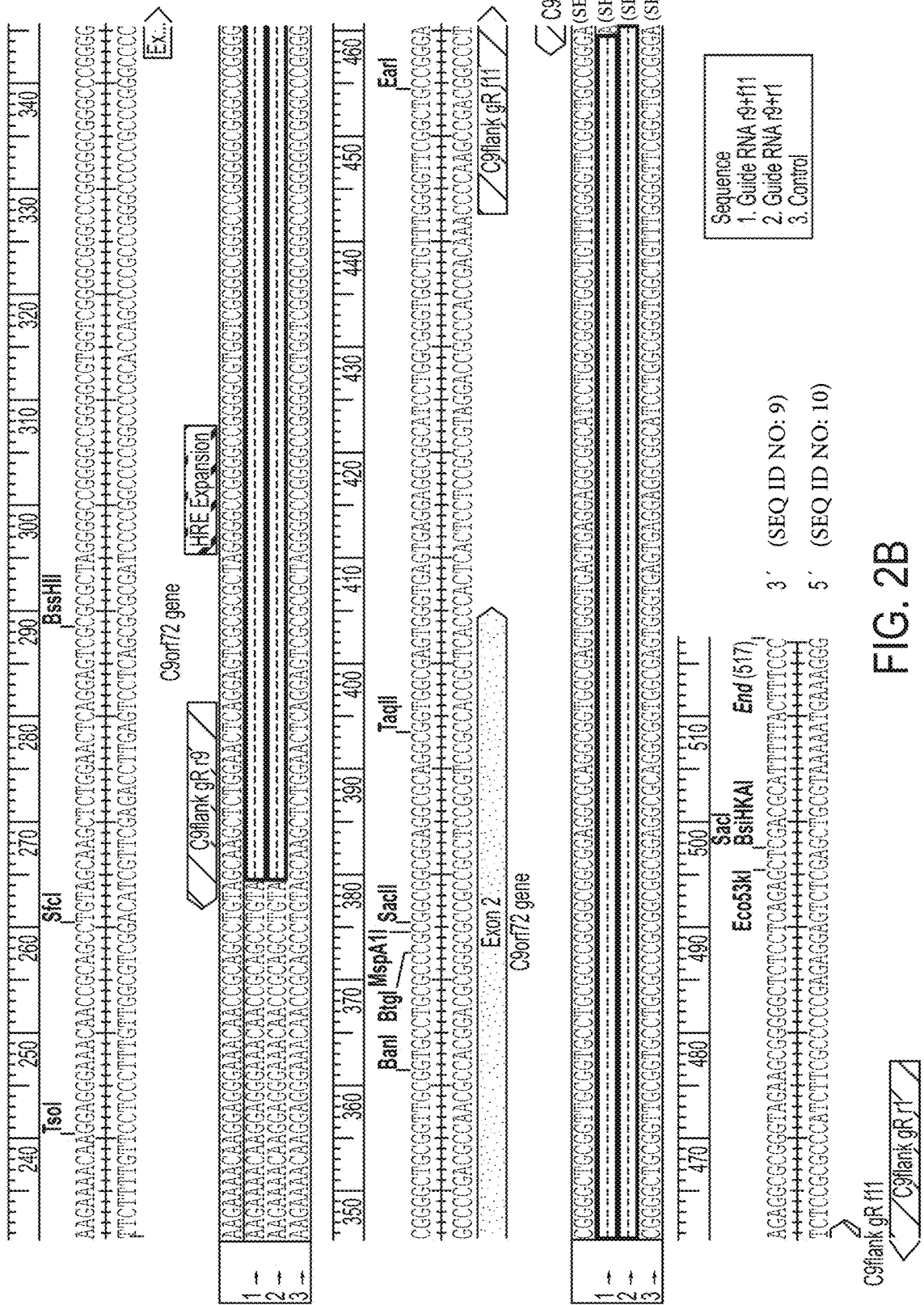

As seen on the gel (FIG. 2A) these four different combination are capable of editing C9 gene in HEK cells, since bands of the anticipated edited size in each of these guide RNA combinations are observed. gRNA f1-r1 and gRNAf1-f11 both have a faint band between 200 and 300 bp, while gRNA r9-f11 and gRNA r9-r1 have a strong band around 320 bp. Both of these bands are absent in the untreated control. However, the combination of r9-f11 and r9-r1 seems to be much more efficient at gene editing, since the edited band is much more intense than f1-r1 and f1-f11 alone. Additionally, the unedited band at 523 bp is almost completely gone from r9-f11 and r9-r1. Bands labeled with arrow heads in FIG. 2A were then extracted and sequenced to ensure that gene editing occurred at the expected locations (FIG. 2B). Based on this data an AAV9 virus containing gRNA r9-r1 and r9-f11 was generated to use for the in vivo studies.

C9ORf72 Gene Editing in Mice Primary Neurons

A mouse model (Bac436) expressing human C9orf72 with 45-65 expanded GGGGCC repeats has been developed. This model contains 6-8 copies of the C9orf72 gene in heterozygous (het) animals and 12-16 copies in homozygous (homo) animals. Additionally, a mouse expressing Cas9 gene, in addition to C9orf72 with the expansion, is observed in this model. In order to determine whether guides will successfully excise the GGGGCC repeat in mice primary neurons, appropriate crosses of the BAC436 mice expressing C9orf72 and Cas9 were set up to produce only heterozygous progeny. Primary neurons were isolated at embryonic day 14 (E14), and cultured appropriately. After 4 days in culture, neurons were either treated with PBS alone, or infected with AAV9 CB-GFP, AAV9 SOD1 guide RNA (control guide), AAV9-CB-GFP-C9gR flank r9-r1, or AAV9-CB-GFP-C9gR flank r9-f11. At 72 hours, 25,000 MOI was recorded and the cells were harvested. The DNA was isolated using QIAGEN™ blood and tissue DNA extraction kit.

Figure 3:
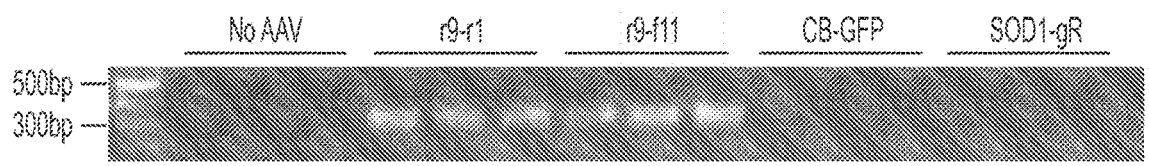
FIG. 3 shows Cas9-mediated C9orf72 $G_4C_2$ editing in mouse primary neurons. Agarose electrophoresis of PCR products amplified by C9Var1-f and C9In1-R primers. The edited PCR products appear around 320 bp, while the unedited DNA is not amplified.

In order to determine whether editing has occurred in these isolated neuronal cells, a PCR reaction was performed using C9Var1-f and C9In1-R (FIGS. 1A and 1B). Without gene editing, these primers fail to amplify through the repeat and no band appears on the gel. When gene editing occurs, the repeat is excised out and primers amplify a single band at 321 bp. In both sets of guides a strong band appearing at the right size is observed, while this band is absent in both non-AAV treated neurons and those transfected with CB-GFP, or SOD1-gR (FIG. 3).

Testing Guide RNA Constructs in Mice Livers

Figure 4:
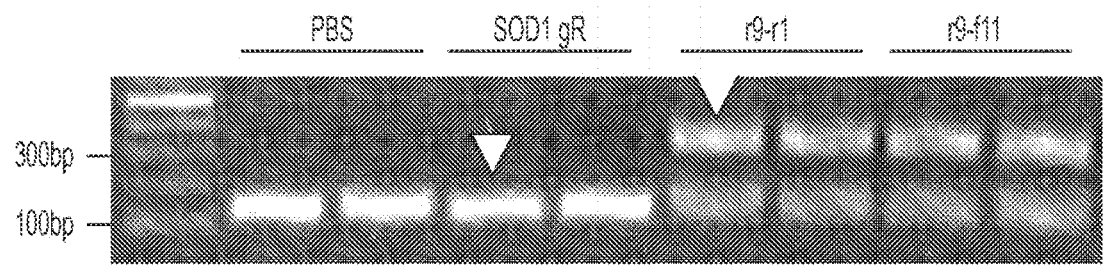
FIG. 4 shows Cas9-mediated C9orf72 $G_4C_2$ editing in vivo confirmed through regular PCR. Agarose electrophoresis of PCR products amplified by C9Var1-f and C9In1-R primers or NoE-F1 and C9In1-R combined in the same well. The edited PCR products are at ~320 bp while unedited PCR products are at ~120 bp.
Figure 5A:
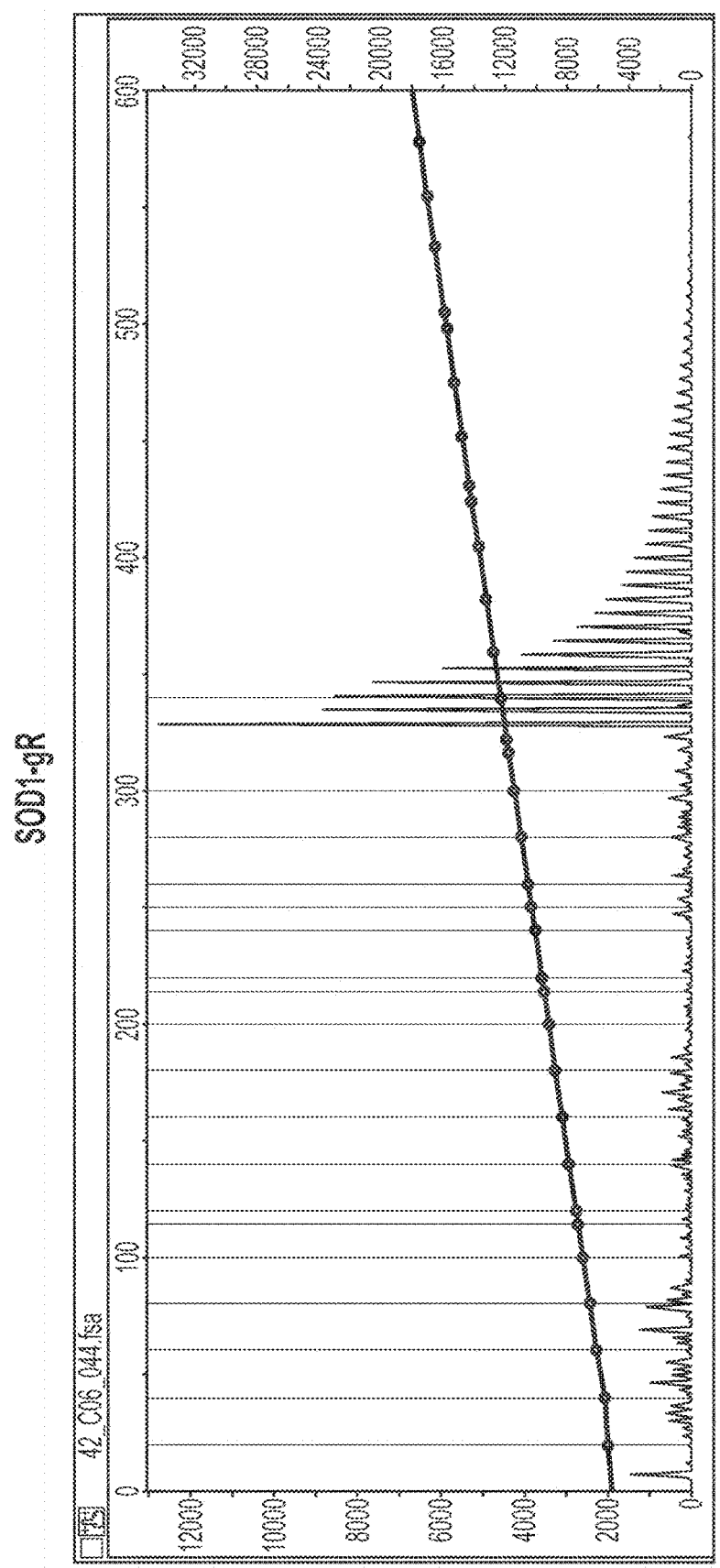
FIGS. 5A to 5D show Cas9-mediated C9orf72 $G_4C_2$ editing in vivo confirmed through Repeat Primed PCR. Electropherograms of Repeat primed PCR products were run through a fragment analyzer and plotted using peak scanner software. The PCR reactions were run using DNA from BAC436 mice tail vein injected with either AAV9 SOD1 guide RNA (FIG. 5A), AAV9-CB-GFP-C9gR flank r9-r1 (FIG. 5B), AAV9-CB-GFP-C9gR flank r9-f11 (FIG. 5C) or uninjected wild type C57BL mice that don't express human C9 (FIG. 5D).
Figure 5B:
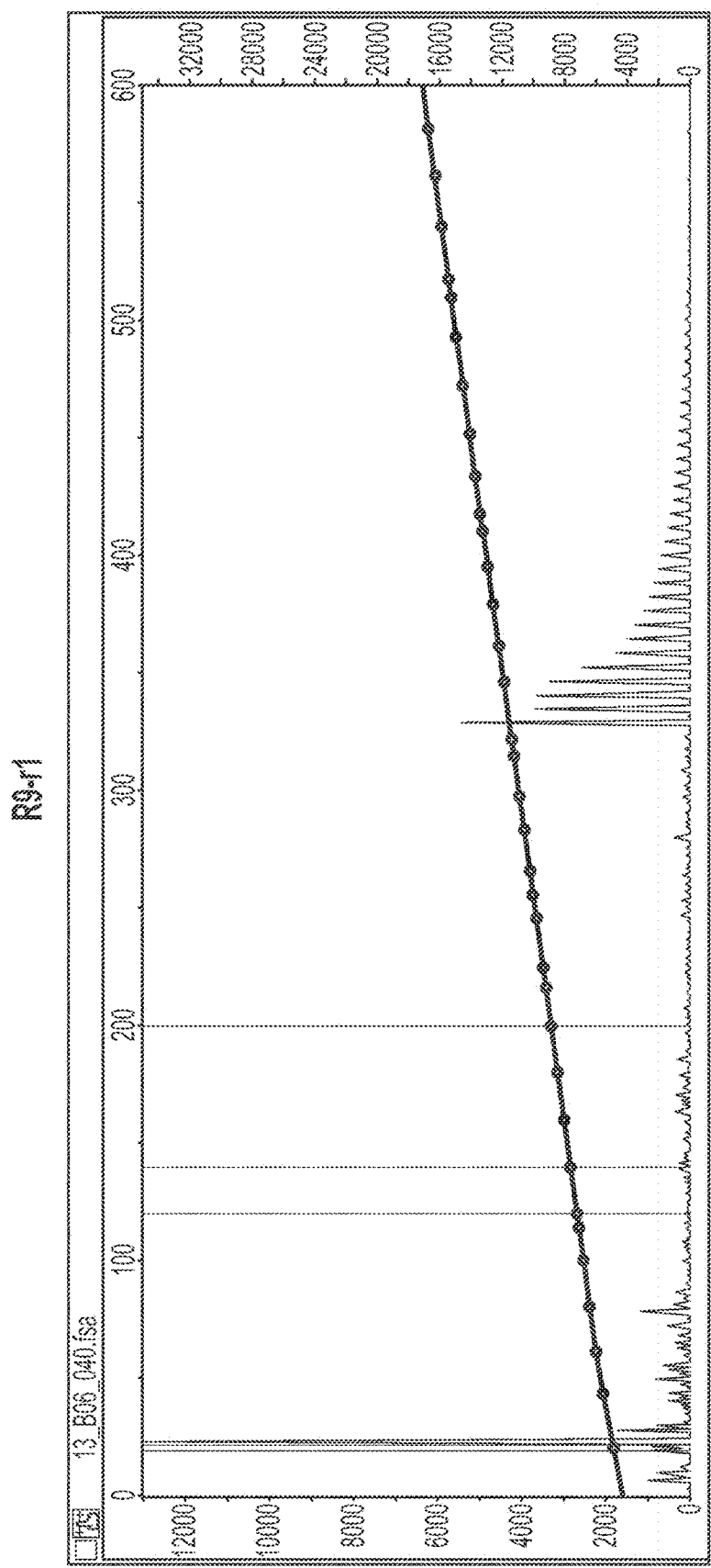
Figure 5C:
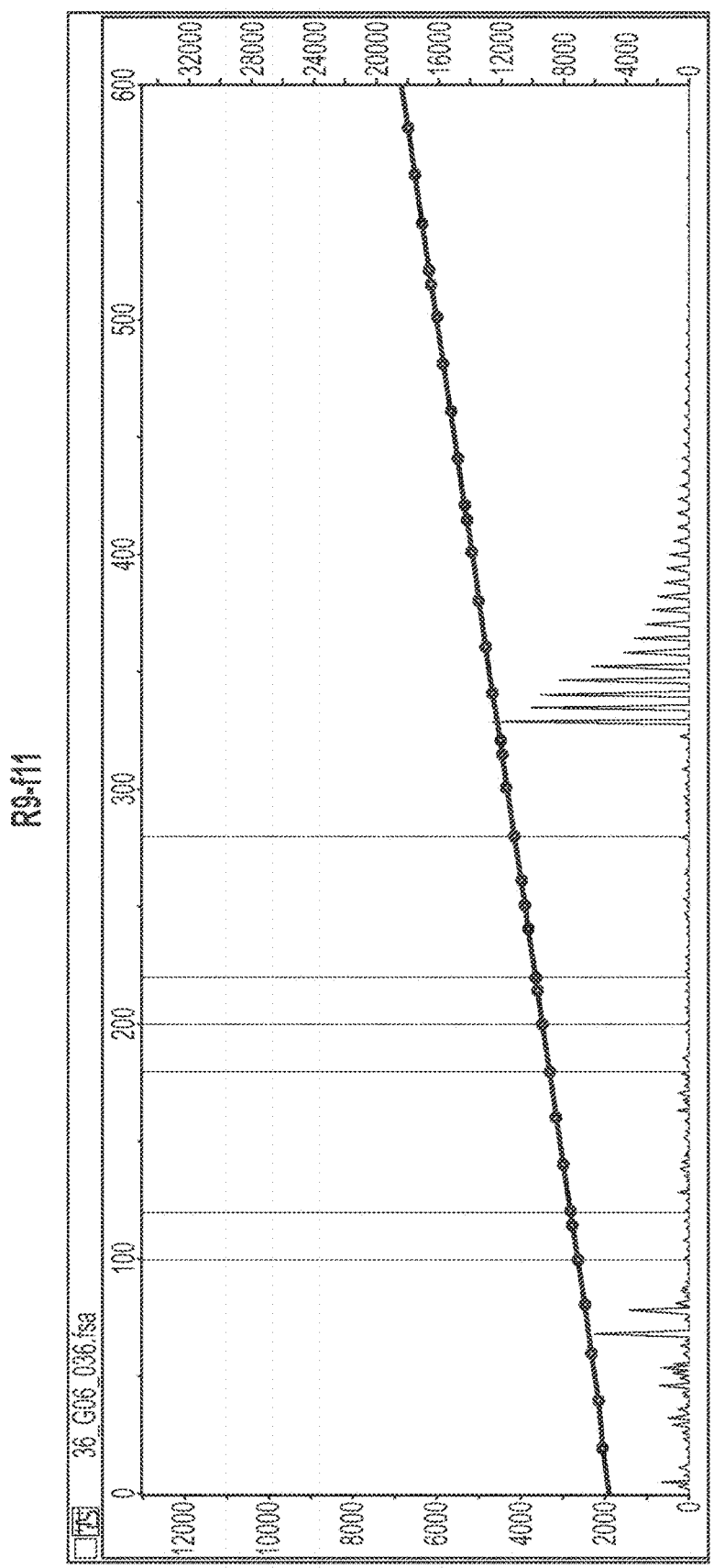
Figure 5D:
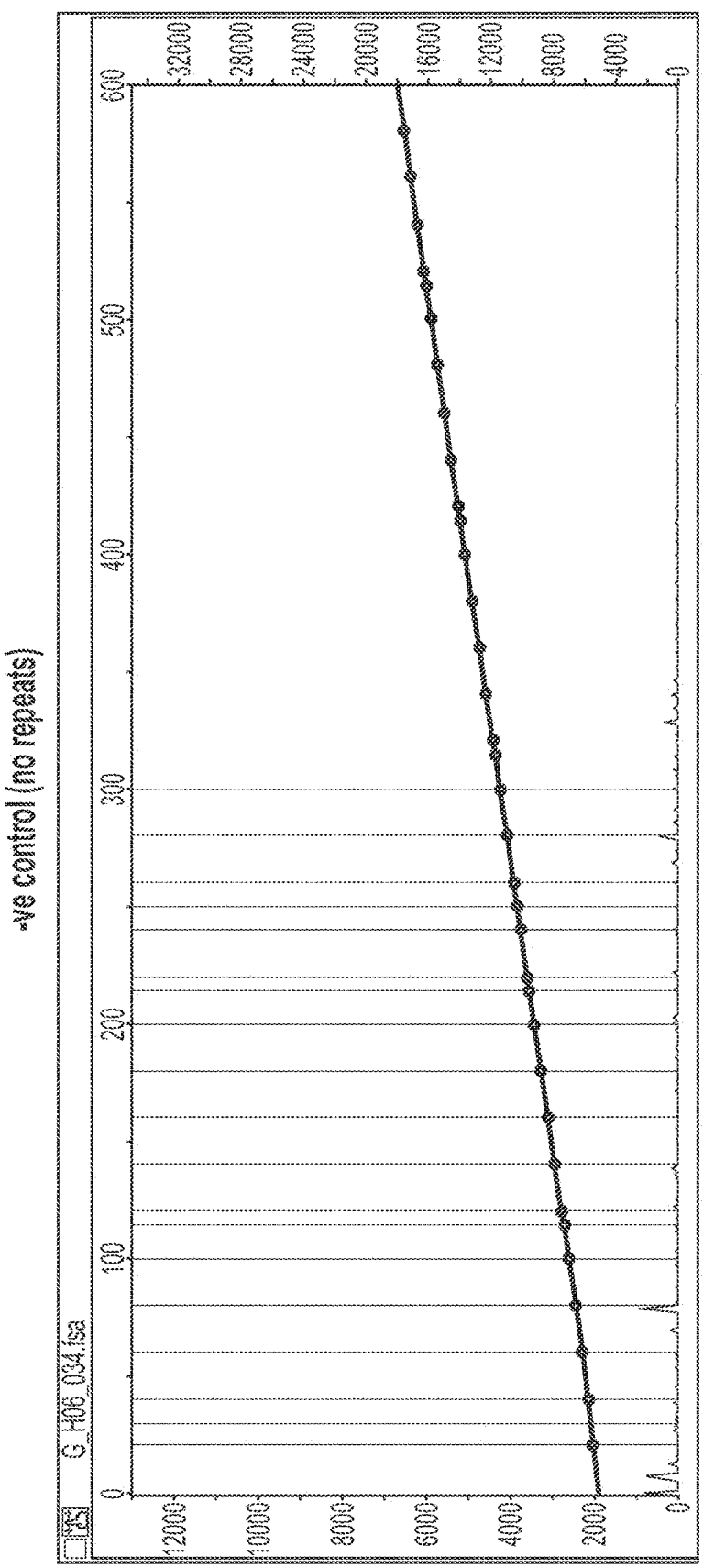

In order to determine whether gene editing is also successful in vivo, four groups of Cas9/+, C9/+mice were tail vein injected with PBS alone, AAV9 SOD1 guide RNA, AAV9-CB-GFP-C9gR flank r9-r1, or AAV9-CB-GFP-C9gR flank r9-f11. Two weeks after injection, mice were sacrificed and tissues were harvested. Since tail vein injection is very efficient at transfecting liver cells, DNA isolated from liver was analyzed. A third primer (NoE-F1) that can amplify unedited DNA, in conjugation with C9In1-R, was designed (FIG. 1B). To reduce competition between C9Var1-f and NoE-F1, two different PCR reactions were run separately with C9Var1-f and C9In1-R or NoE-F1 and C9In1-R. Products from these two PCRs were mixed and run on the same gel (FIG. 4). A 321 bp band appears in samples from mice injected with AAV9-CB-GFP-C9gR flank r9-r1 and AAV9-CB-GFP-C9gR flank r9-f11, but not from mice injected with AAV9 SOD1 guide RNA or PBS alone (FIG. 4). Moreover, the 100 bp amplified by NoE-F1 and C9In1-R from unedited DNA was much less intense in r9-r1 and r9-f11 mice in comparison to control mice. The labeled bands were isolated and sequenced to confirm that the correct size gene editing products were made.

To further elucidate editing, a Repeat Primed PCR was performed using a FAM-tagged C9Var1-f and c9ccccggLCM13F_MRX-R1b. The latter is a reverse primer that recognizes and binds the GGGGCC repeat. This form of PCR reaction produces different sized fragments based on where in the repeat the reverse primer binds and starts the amplification. These fragments were then analyzed on a fragment analyzer to produce an electropherogram where each peak reflects a different sized fragment and its intensity reflects fragment abundance. As the primer binds deeper into the repeat, it becomes more difficult to amplify and thus the intensity of peaks on the electropherogram decreases with larger fragments. These fragments can only be amplified in unedited DNA, and the shortest most intense fragment is around 330 bp in size. The electropherograms of the Repeat primed PCR products for AAV9 SOD1 guide RNA, AAV9-CB-GFP-C9gR flank r9-r1, AAV9-CB-GFP-C9gR flank r9-f11, and uninjected wild type C57BL mice that don't express human C9 are shown in FIGS. 5A-5D, respectively. The results confirm Cas9-mediated C9orf72 G4C2 editing in vivo.

Example 2: Induction of Non-Sense Mediated Decay of C9orf72 Transcripts

Figure 6A:
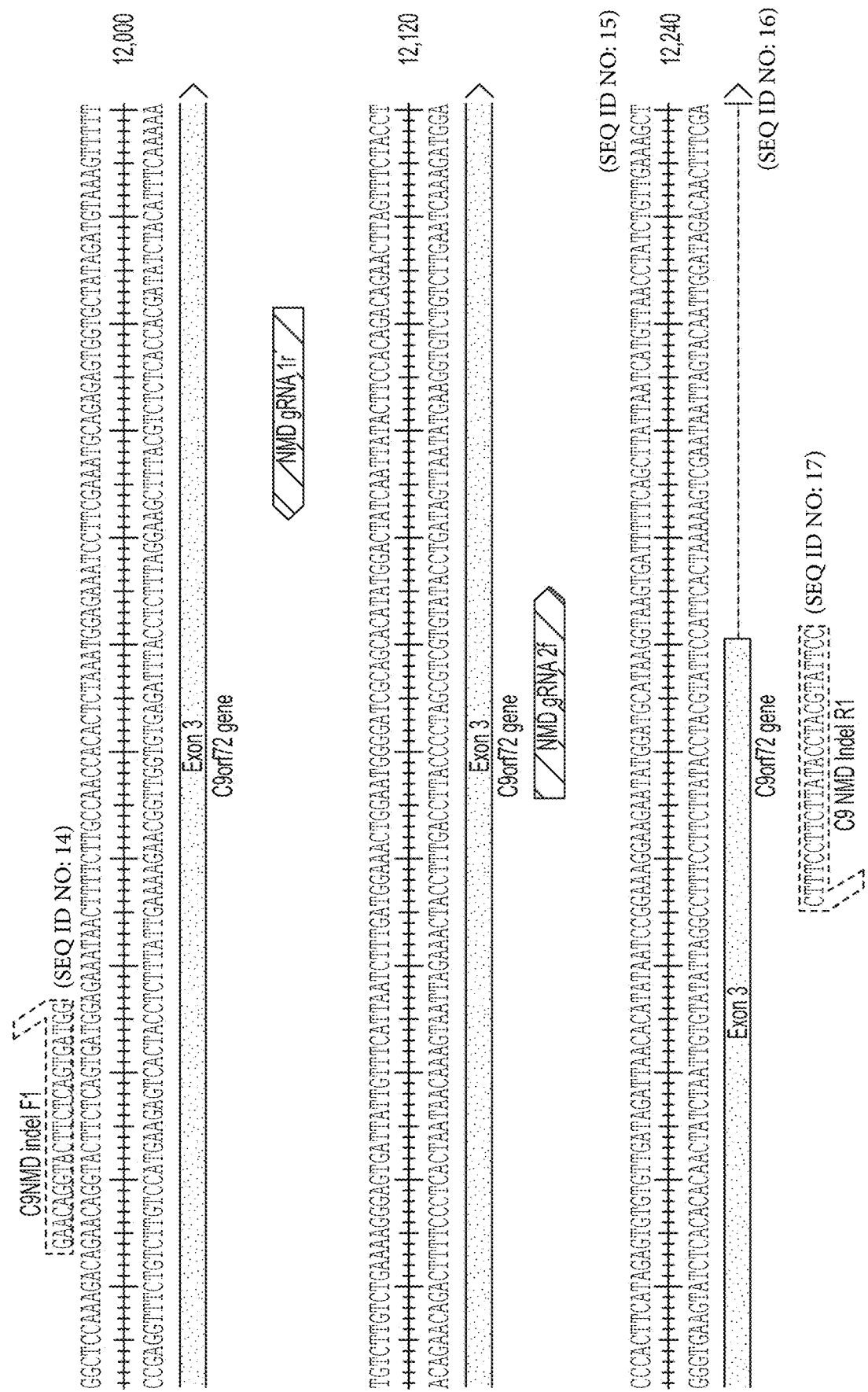
FIGS. 6A to 6C show representative data described in Example 2.
Figures 6B, 6C:
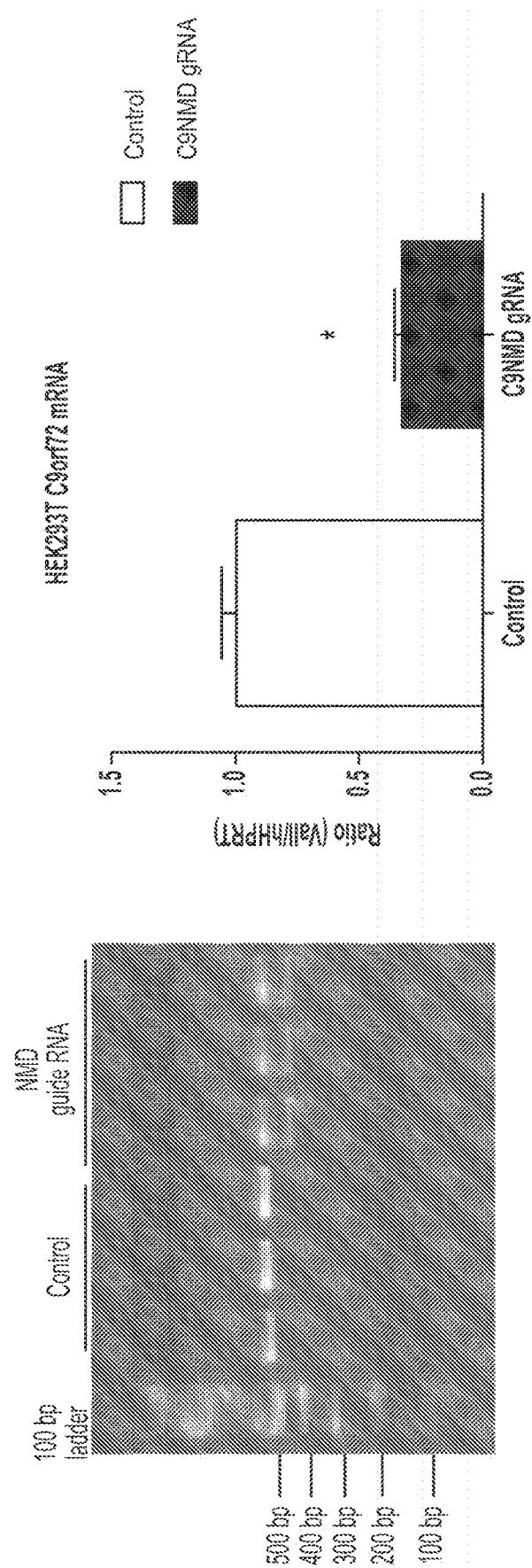

In this example, guide RNAs were designed to target exon 3 after the ATG initiation codon of C9orf72 (Table 2). The strategy was to introduce small indels that will lead to early termination codon, thus inducing non-sense mediated decay of C9orf72 transcripts to reduce RNA foci and dipeptide formation. FIG. 6A shows the human C9orf72 gene sequence of exon 3 with the locations of the non-sense mediated decay (NMD) guide RNA 1r and 2f and the location and sequence of PCR indel analysis primers C9NMD Indel F1 and R1 marked. FIG. 6B shows the results of agarose gel electrophoresis of the PCR products amplified by the C9NMD-Indel F1 and R1 PCR primers. In this example, HEK293T cells were transfected with LV-SpCas9 (Control) or LV-NMDgR-SpCas9 plasmid (2 µg) in triplicate. FIG. 6C shows the results of digital droplet PCT (ddPCR) analysis of the C9orf72 RNA levels from FIG. 6B.

TABLE 2

Guide RNAs generated for "Non-sense mediated decay."

| guide RNA | guide RNA sequence | SEQ ID NO: |
|---|---|---|
| NMD gRNA 1r | UCGAAAUGCAGAGAGUGGUG | 5 |
| NMD gRNA 2f | AAUGGGGAUCGCAGCACAUA | 6 |

Example 3: Direct Visualization of C9ORf72 Gene Editing in Primary Neurons

Figure 7:
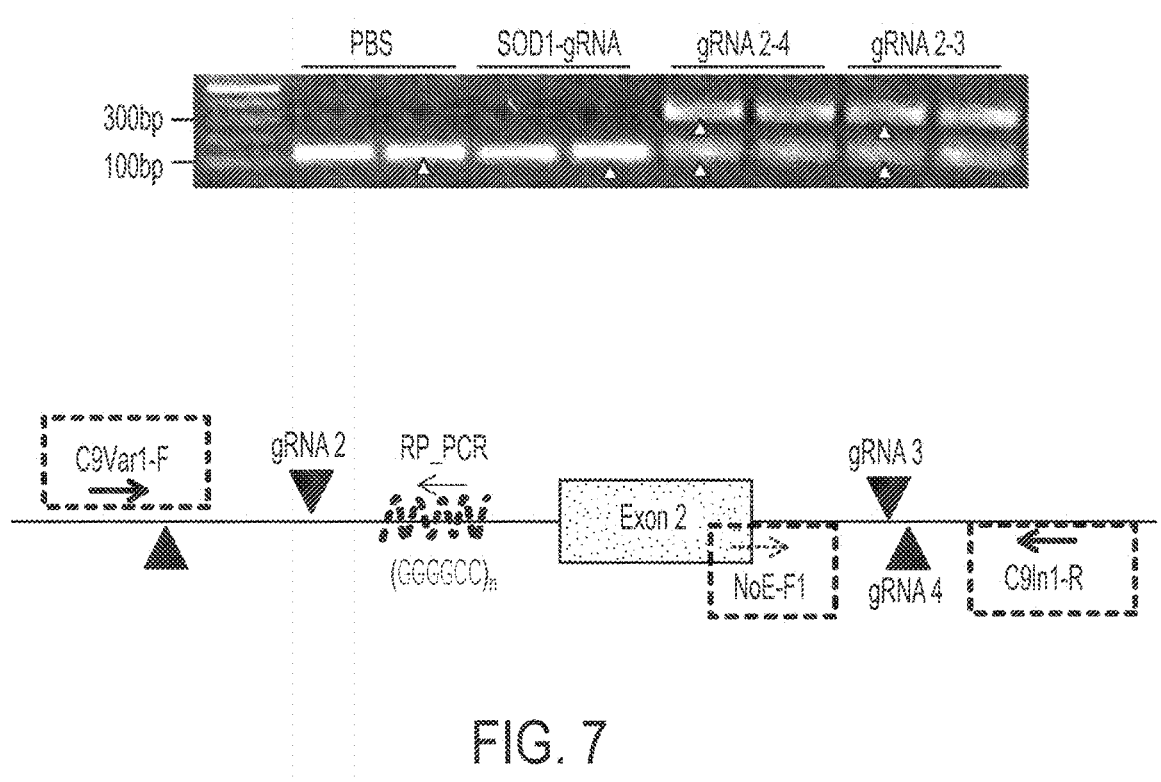
FIG. 7 shows representative data for gene editing in mice injected via tail vein. Guide strands were tested through tail vein injection of BAC111 mice expressing both C9/Cas9 to determine whether they are functional in vivo. The liver of injected mice were dissected and genomic DNA was extracted and a two PCR reactions were run. The top panel indicates gene editing occurs after injection of gRNA2-4 and gRNA2-3 but not PBS or SOD1-gRNA. As depicted in the bottom panel, one reaction (using primers C9Var1F and C9IndR) amplifies only edited DNA, since the repeat is GC rich and a polymerase cannot amplify through the repeat; thus, a band indicates edited DNA. The other reaction (using primers NoE-F1 and C9IndR) can only amplify unedited DNA.
Figure 8A:
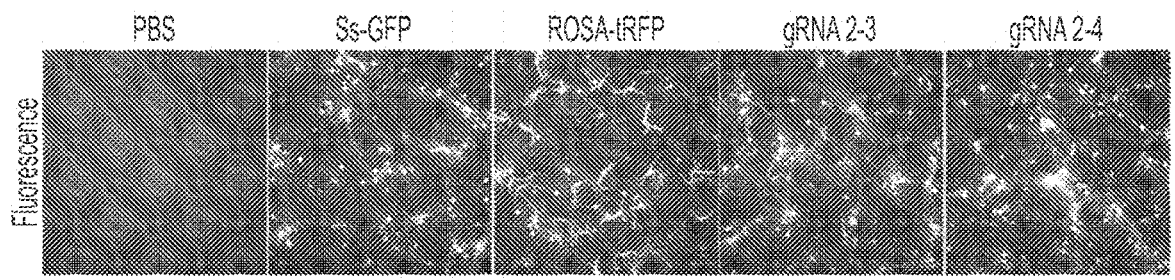
FIGS. 8A to 8B show gene editing in cultured primary neurons from BAC111 expressing C9orf72 and Cas9.

A mouse model (BAC111) expressing human C9orf72 with 45-65 expanded GGGGCC repeats has been developed. This model contains 6-8 copies of the C9orf72 gene in heterozygous (het) animals and 12-16 copies in homozygous (homo) animals. Additionally, this mouse model expresses Cas9, in addition to C9orf72 with the expansion. In order to determine whether guides successfully excise the GGGGCC repeat in mice primary neurons, appropriate crosses of the BAC111 mice expressing C9orf72 and Cas9 were set up to produce only heterozygous progeny. Primary neurons were isolated at embryonic day 14 (E14), and cultured appropriately. After 4 days in culture, neurons were either treated with PBS alone, or infected with AAV9 single-stranded-GFP (ss-GFP), AAV9-ROSA-tRFP guide RNA (control guide), AAV9-GFP-C9gR flank gRNA 2 & 3, or AAV9-GFP-C9gR flank gRNA 2 & 4. At 72 hours, 25,000 MOI was recorded and the cells were harvested. The DNA was isolated using QIAGEN™ blood and tissue DNA extraction kit. PCR results are shown in FIG. 7. The cultured primary neurons were imaged for GFP or RFP fluorescence to visualize the incorporation of AAV9-gRNA constructs to into primary neurons (FIG. 8A).

Figure 8B:
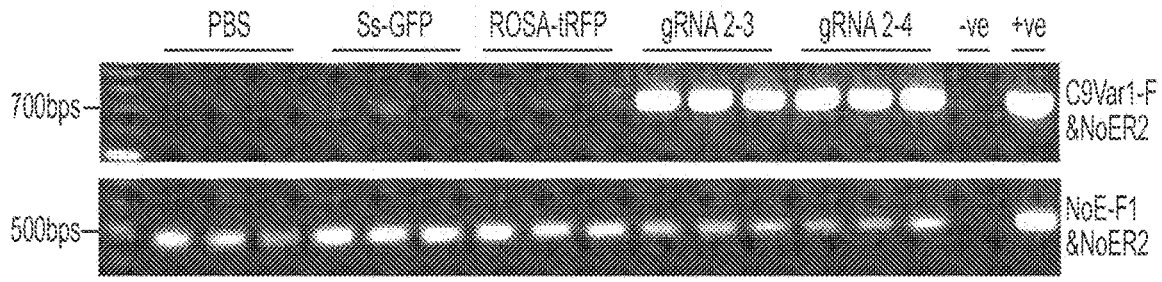
Figure 8B:
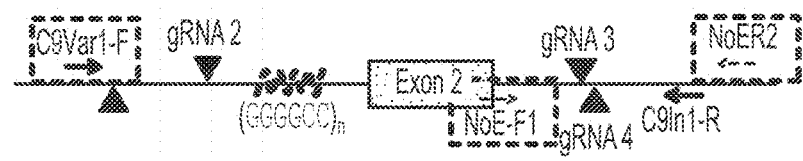

In order to determine whether editing occurred in these isolated neuronal cells, a PCR reaction was performed using C9Var1-F and NoER2 primers (FIG. 8B). Without gene editing, these primers fail to amplify through the repeat and no band appears on the gel. When gene editing occurs, the repeat is excised out and primers amplify a single band at about 720 base pairs. In both sets of guides a strong band appearing at the right size is observed, while this band is absent in both non-AAV treated neurons (PBS) and those transfected with ss-GFP, or ROSA-tRFP (FIG. 8B). In order to estimate the level of unedited DNA, a PCR reaction was performed using NoE-F1 and NoER2 (FIG. 8B). A band of about 500 base pairs appears on a gel when gene editing has not occurred. Control gene editing conditions (PBS, ss-GFP, or ROSA-tRFP) produced an intense band at about 500 base pairs, while both sets of gRNA 2 & 3 and gRNA 2 & 4 guides have less unedited samples.

Figure 9:
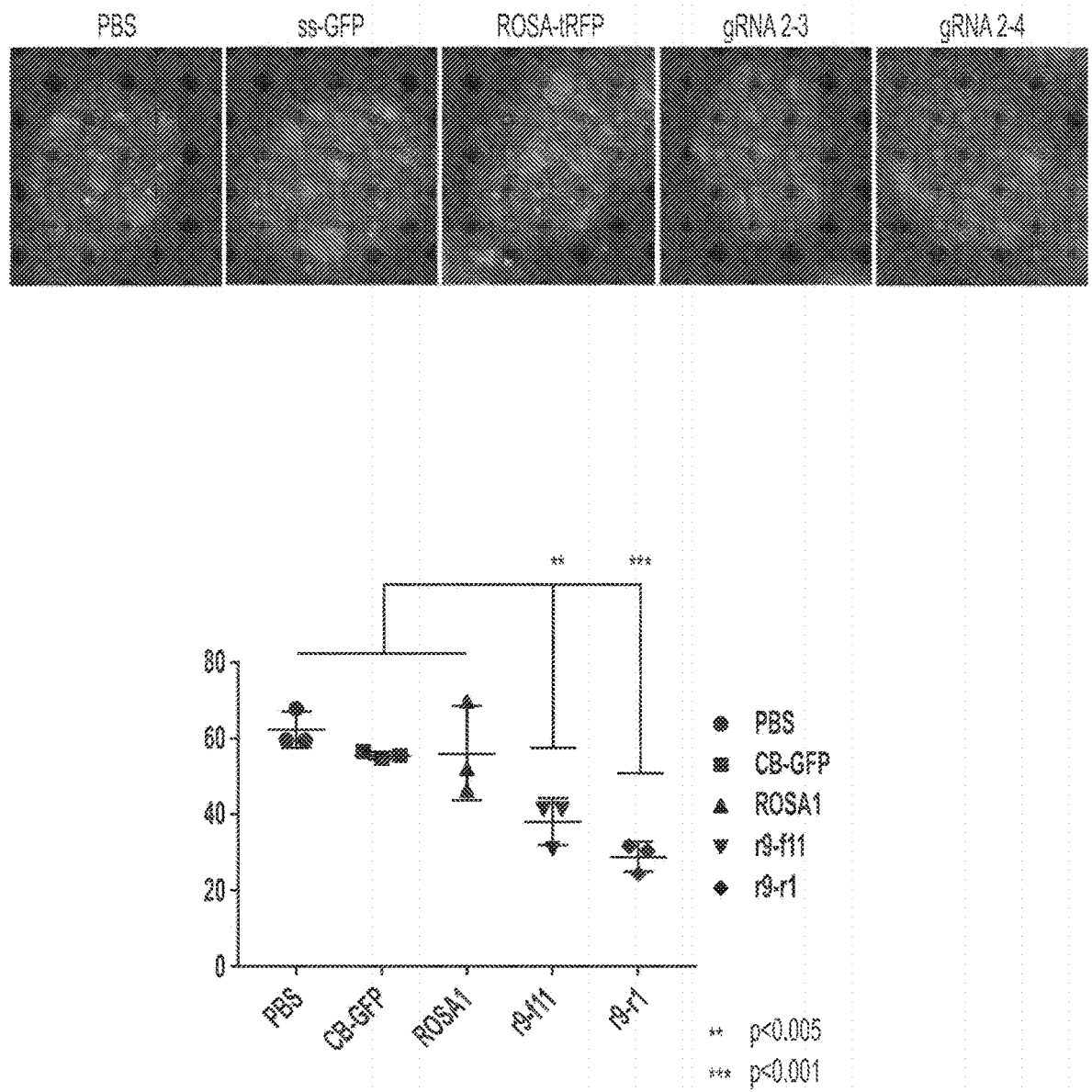
FIG. 9 shows direct visualization and quantification of gRNAs bound to unedited DNA from primary cultured neurons isolated from BAC111 mice expressing C9/Cas9 by fluorescence in-situ hybridization (FISH). Almost 55-60% of unedited cells have foci many with more than 10 foci. Edited cells exhibit foci in about 35-40% of cells, and the number of foci is dramatically reduced as well.

To directly visualize gene editing, cultured primary neurons from BAC111 mice expressing human C9orf72 and Cas9 were isolated and treated with PBS, AAV9-ss-GFP, AAV9-ROSA-tRFP, AAV9-gRNA 2 & 3, AAV9-gRNA 2 & 4 as above. Fluorescence in situ hybridization (FISH) was used to visualize unedited C9orf72 RNA (punctate staining, e.g., foci) and nuclei were stained with DAPI (FIG. 9). Almost 55-60% of unedited cells have more than ten foci, while edited cells exhibit significantly less in only 35-40% of cells (FIG. 9).

Example 4: Exogenous Cas9 Promotes C9ORf72 Gene Editing in Primary Neurons

Figure 10A:
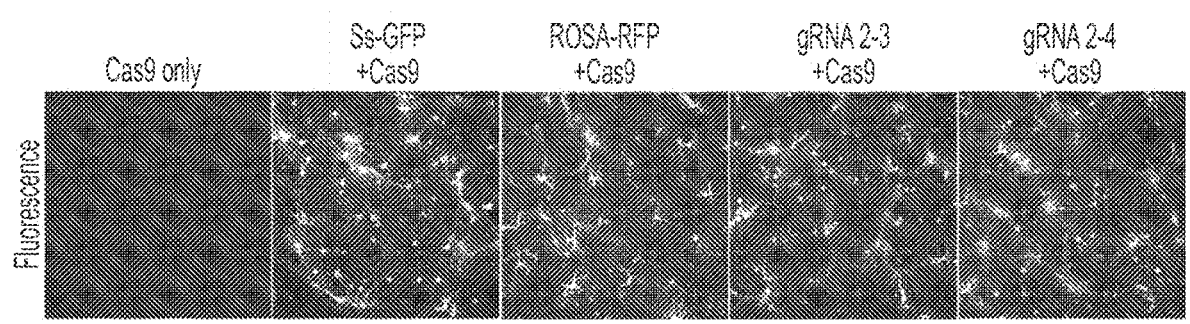
FIGS. 10A to 10B show gene editing in cultured primary neurons from BAC111 expressing C9orf72, but not Cas9.

To directly test whether C9orf72 excision of GGGGCC repeats requires endogenous Cas9 expression, BAC111 mouse models expressing C9orf72 and not Cas9 were produced. Primary neurons were isolated at embryonic day 14 (E14), and cultured appropriately. After 4 days in culture, neurons were supplemented with Cas9 and either treated with Cas9 alone, or infected with AAV9-ss-GFP+Cas9, AAV9-ROSA-RFP+Cas9 (control guide), AAV9-GFP-C9gR flank gRNA 2 & 3, or AAV9-GFP-C9gR flank gRNA 2 & 4. At 72 hours, 25,000 MOI was recorded and the cells were harvested. The DNA was isolated using QIAGEN™ blood and tissue DNA extraction kit. The cultured primary neurons were imaged for GFP or RFP fluorescence to visualize the incorporation of AAV9-gRNA constructs to into primary neurons (FIG. 10A).

Figure 10B:
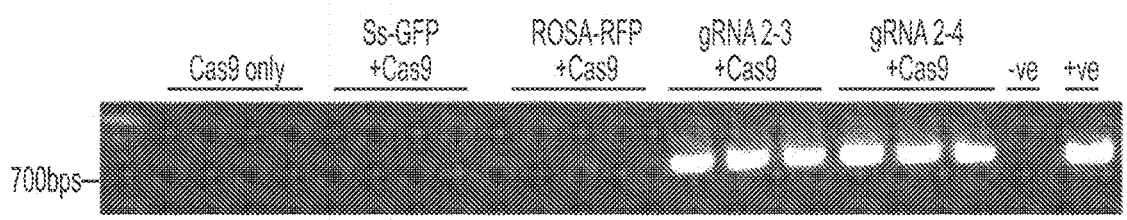
Figure 10B:
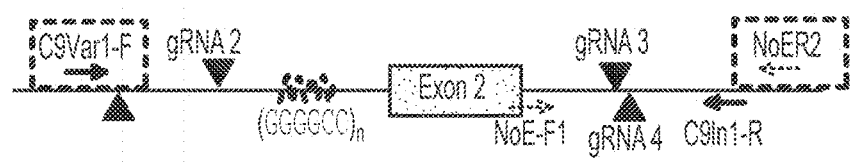

PCR amplification of edited DNA from cultured neurons was performed. Briefly, edited DNA was amplified by PCR with C9Var1-F & NoER2 (FIG. 10B). Amplification bands occur only in edited cells (e.g., cells treated with AAV9-gRNA 2-3+Cas9, or AAV9-gRNA 2-4+Cas9), as shown in FIG. 10B.

Figure 11:
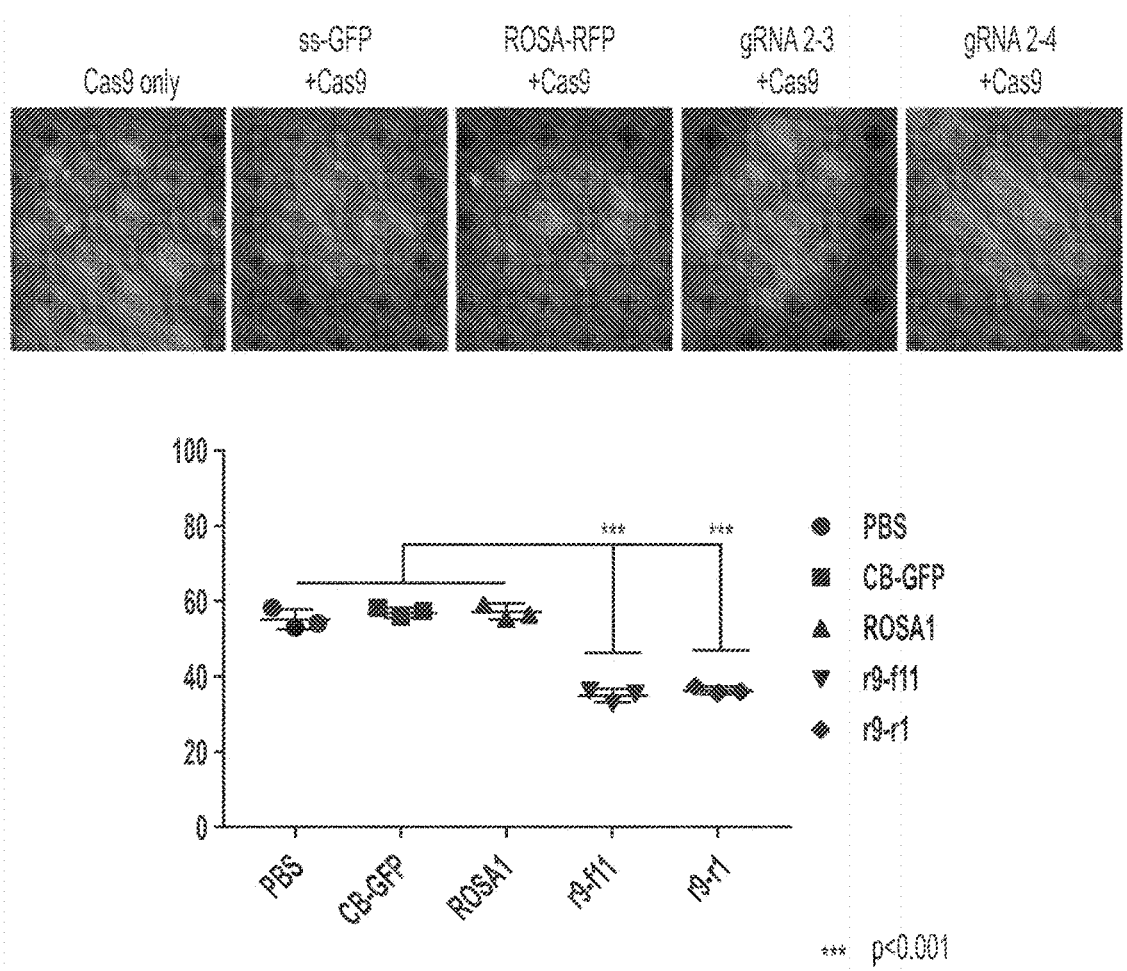
FIG. 11 shows direct visualization and quantification of gRNAs bound to unedited DNA from primary cultured neurons isolated from BAC111 mice expressing C9 by FISH. Around 55-60% of cells have foci when unedited (Cas9 only, single stranded GFP, ROSA); edited cells are reduced to 35-40%. Both gRNA pairs result in a significantly different reduction.

FIG. 11 shows direct visualization and quantification of gRNAs bound to unedited DNA from primary cultured neurons isolated from BAC111 mice expressing C9 by FISH. Around 55-60% of cells have foci when unedited (Cas9 only, single stranded GFP, ROSA). Foci in edited cells were reduced to 35-40%. Treatment with both gRNA pairs resulted in a significantly different reduction.

Figure 12:
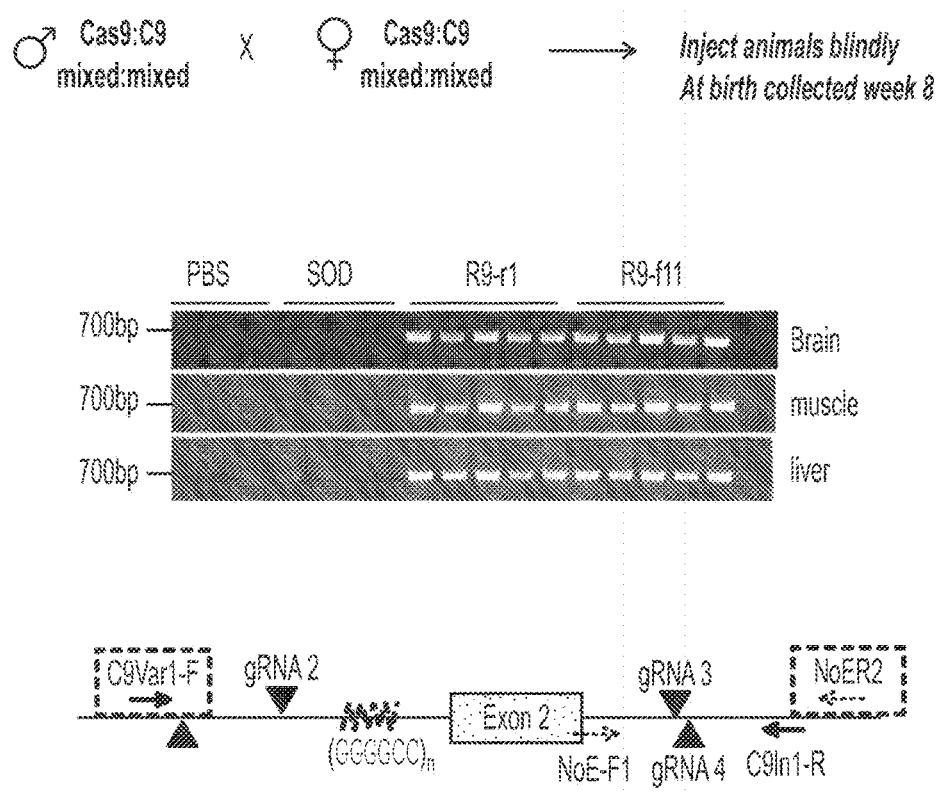
FIG. 12 shows gene editing in vivo in BAC111 mice expressing C9/Cas9 injected with PBS, SOD gRNA (control), R9-r1 (gRNA 2 & 4), or R9-f11 (gRNA 2 & 3). Brain, muscle, and liver tissue samples taken after 8 weeks each demonstrated gene editing with gRNA 2 & 3 and gRNA 2 & 4 guides, but not PBS and control SOD gRNA.

Tissue distribution of gene editing constructs (e.g., rAAVs) was examined. FIG. 12 shows gene editing in vivo in BAC111 mice expressing C9/Cas9 injected with PBS, SOD gRNA (control), R9-r1 (gRNA 2 & 4), or R9-fl1 (gRNA 2 & 3). Brain, muscle, and liver tissue samples taken after 8 weeks each demonstrated gene editing with gRNA 2 & 3 and gRNA 2 & 4 guides, but not PBS and control SOD gRNA.

Figure 13:
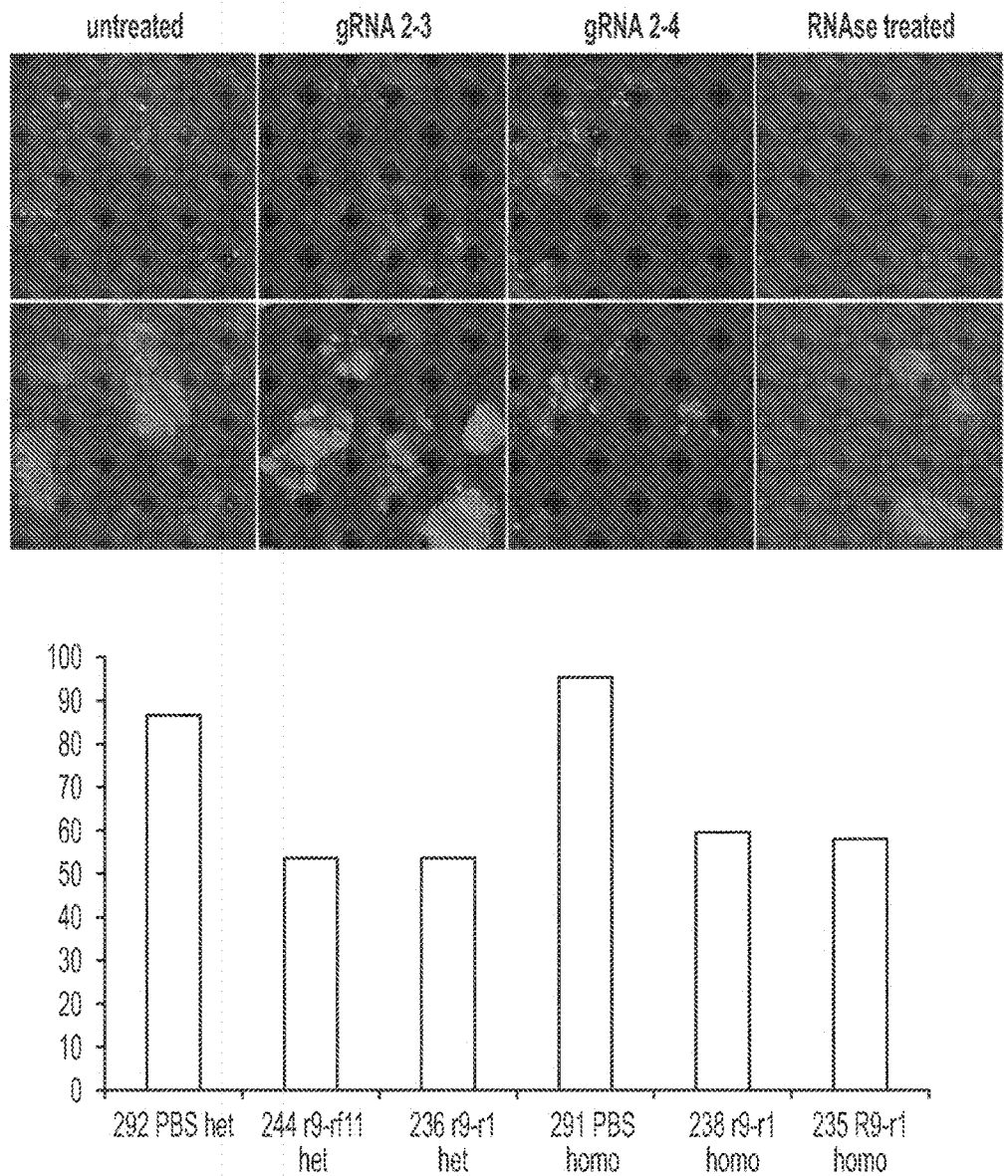
FIG. 13 shows FISH data (sense direction) on frontal sections of CAC111 mice that were facially injected at p1-2. The top panel shows a fluorescence micrograph indicating a reduction in number of foci in edited cells compared to untreated and control cells. The bottom panel shows data indicating the reduction is consistent for heterozygous and homozygous mice.

FIG. 13 shows FISH data (sense direction) on frontal sections of CAC111 mice that were facially injected at p1-2. The top panel shows a fluorescence micrograph indicating a reduction in number of foci in edited cells compared to untreated and control cells. The bottom panel shows data indicating the reduction is consistent for heterozygous and homozygous mice.

Figure 14A:
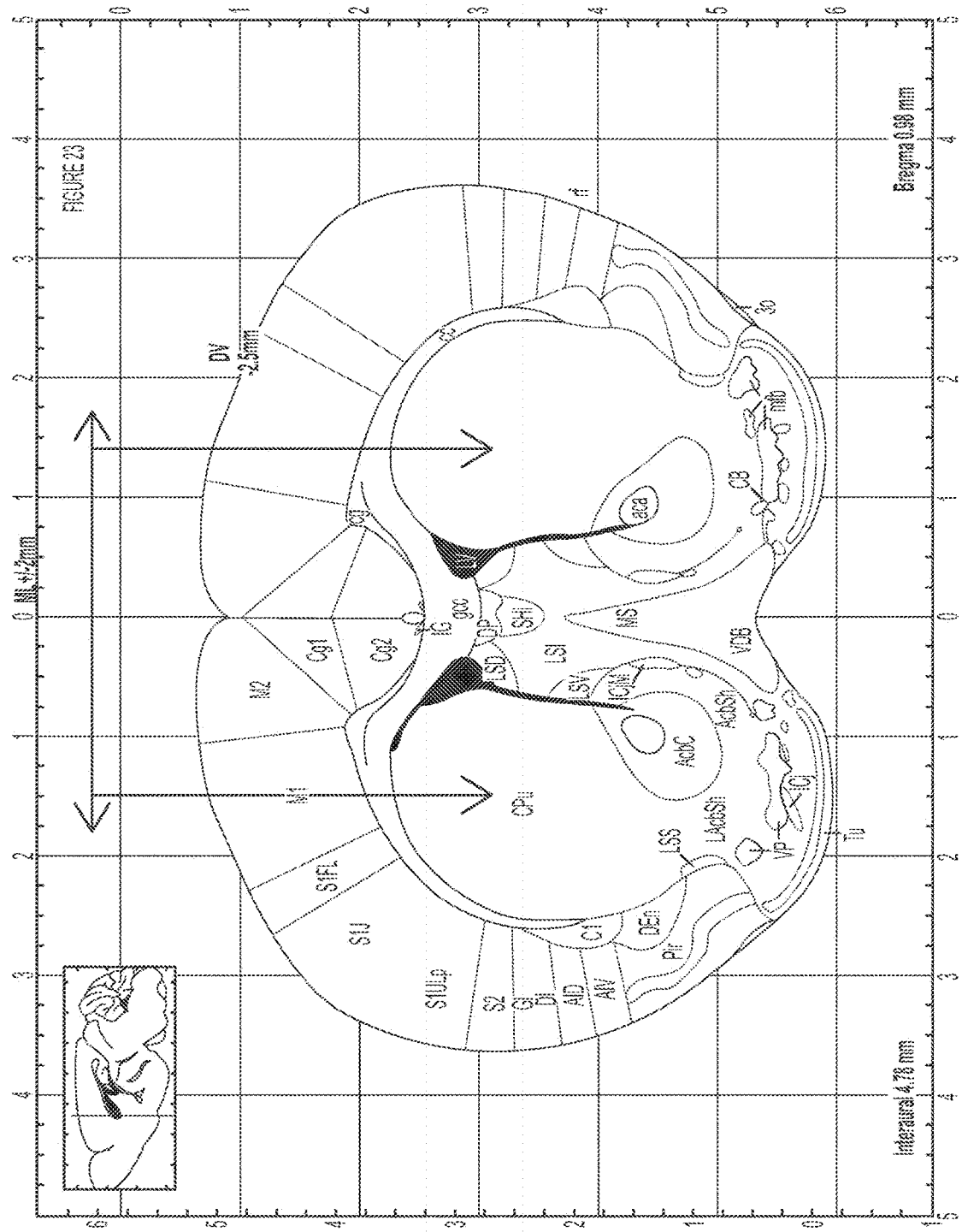
FIGS. 14A-14B show gene editing through stereotaxic striatal brain injections in Baloh and BAC111 mice.
Figure 14A:
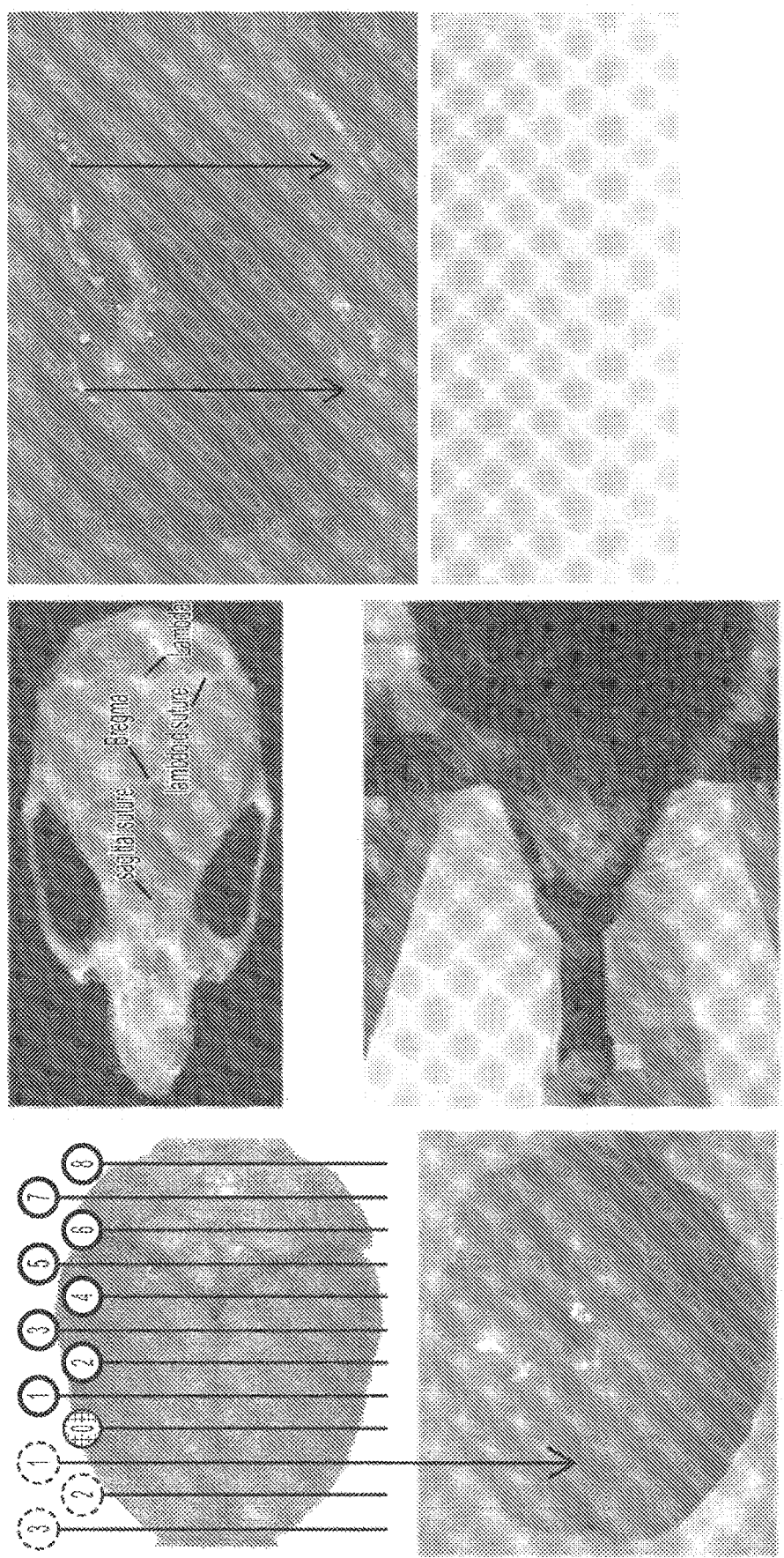
Figure 14B:
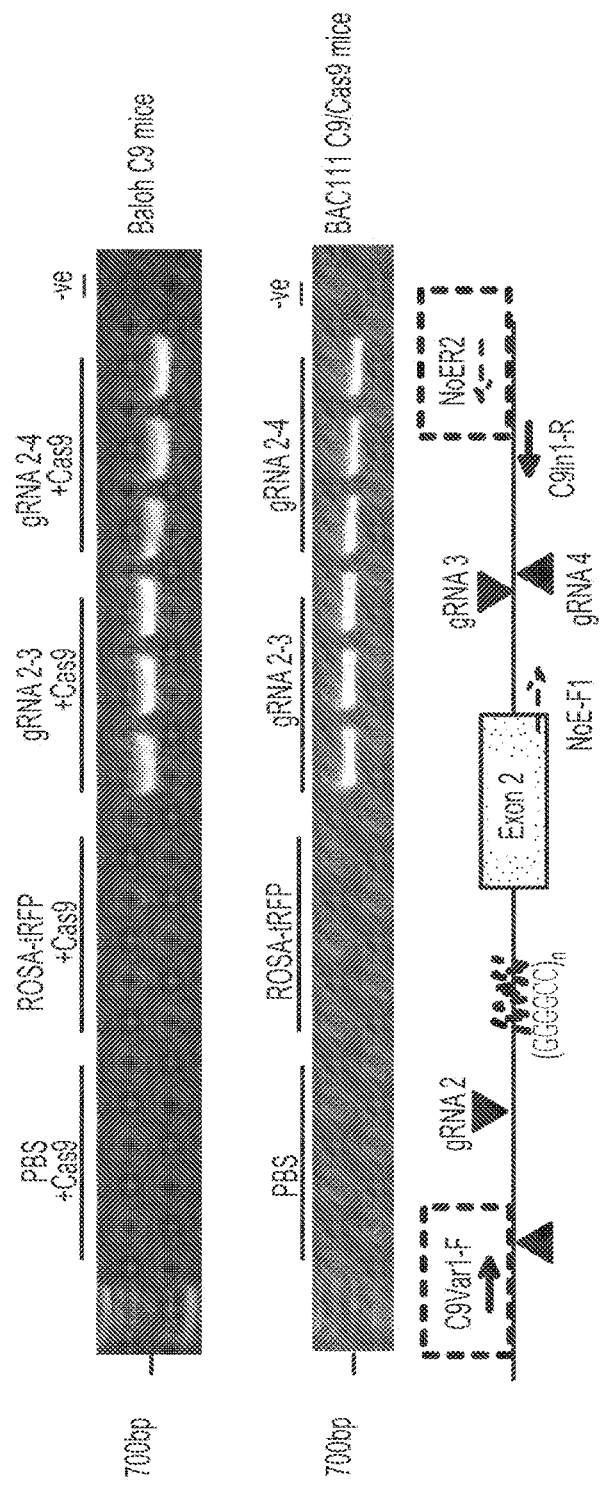

FIGS. 14A-14B show gene editing through stereotaxic striatal brain injections in Baloh and BAC111 mice. FIG. 14A shows the injection site and the brain slice used for tissue isolation. FIG. 14B shows that injection of PBS+Cas9, ROSA-tRFP+Cas9, gRNA 2 & 3+Cas9, gRNA 2 & 4+Cas9 promotes gene editing in Baloh C9 mice and BAC111 C9/Cas9 mice.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A recombinant adeno-associated virus (rAAV) comprising:
   (i) a nucleic acid comprising a transgene encoding a first guide RNA (gRNA) and a second gRNA that each specifically hybridize to a target nucleic acid sequence flanking opposite sides of a $G_4C_2$ repeat of a C9ORF72 gene, flanked by adeno-associated virus (AAV) inverted terminal repeats (ITRs); and
   (ii) at least one AAV capsid protein,
   wherein the first gRNA consists of SEQ ID NO: 1 and the second gRNA consists of SEQ ID NO: 3.

2. The rAAV of claim 1, wherein the at least one capsid protein is of a serotype selected from AAV1, AAV2, AAV3, AAV4, AAV5, AAV6, AAV7, AAV8, AAV9, or a variant of any of the foregoing.

3. The rAAV of claim 1, wherein the at least one capsid protein is an AAV9 capsid protein.

4. A composition comprising the rAAV of claim 1, and a recombinant gene editing protein, wherein the recombinant gene editing protein is a CRISPR/Cas protein.

5. The composition of claim 4, wherein the recombinant gene editing protein is encoded by an rAAV vector.

6. The rAAV of claim 1, wherein the AAV ITRs are AAV2 ITRs, AAV3 ITRs, AAV4 ITRs, AAV5 ITRs, AAV6 ITRs, AAV7 ITRs, AAV8 ITRs, or AAV9 ITRs.

7. The rAAV of claim 1, wherein the transgene comprises a promoter.

8. The rAAV of claim 7, wherein the promoter is a chicken beta-actin (CB) promoter.

9. The composition of claim 4, wherein the CRISPR/Cas protein is a Cas9 protein.

* * * * *

SEQUENCE LISTING

```
<160> NUMBER OF SEQ ID NOS: 17

<210> SEQ ID NO 1
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 1
gggguucggc ugccgggaag                                                20

<210> SEQ ID NO 2
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 2
ggaagaggcg cggguagaag                                                20

<210> SEQ ID NO 3
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 3
guagcaagcu cuggaacuca                                                20

<210> SEQ ID NO 4
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 4
ugcucucaca guacucgcug                                                20

<210> SEQ ID NO 5
<211> LENGTH: 20
<212> TYPE: RNA
<213> ORGANISM: Artificial Sequence
<220> FEATURE:
<223> OTHER INFORMATION: Synthetic Polynucleotide
```

```
<400> SEQUENCE: 5
ucgaaaugca gagaguggug                                                     20

<210> SEQ ID NO 6
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 6 aaugggauc gcagcacaua                                                      20

<210> SEQ ID NO 7
<211> LENGTH: 650
<212> TYPE: DNA
<213> ORGANISM: Artificial Sequence
<220> FEATURE:
<223> OTHER INFORMATION: Synthetic

<400> SEQUENCE: 7
tgccccgccc catttcgcta gcctcgtgag aaaacgtcat cgcacataga aaacagacag         60
acgtaaccta cggtgtcccg ctaggaaaga gaggtgcgtc aaacagcgac aagttccgcc        120
cacgtaaaag atgacgcttg gtgtgtcagc cgtccctgct gcccggttgc ttctcttttg        180 ggggcgggt  ctagcaagag caggtgtggg tttaggaggt gtgtgttttt gttttttccca       240 ccctctctcc ccactacttg ctctcacagt actcgctgag ggtgaacaag aaaagacctg        300
ataaagatta accagaagaa acaaggagg gaaacaaccg cagcctgtag caagctctgg         360
aactcaggag tcgcgcgcta ggggccgggg ccggggccgg ggcgtggtcg gggcgggccc        420 ggggcgggc  ccggggcggg gctgcggttg cggtgcctgc cccgcggcg  gcggaggcgc        480 aggcggtggc gagtgggtga gtgaggaggc ggcatcctgg cgggtggctg tttgggttc         540 ggctgccggg aagaggcgcg ggtagaagcg ggggctctcc tcagagctcg acgcattttt        600
actttccctc tcatttctct gaccgaagct gggtgtcggg ctttcgcctc                   650

<210> SEQ ID NO 8
<211> LENGTH: 650
<212> TYPE: DNA
<213> ORGANISM: Artificial Sequence
<220> FEATURE:
<223> OTHER INFORMATION: Synthetic

<400> SEQUENCE: 8
gaggcgaaag cccgacaccc agcttcggtc agagaaatga gagggaaagt aaaaatgcgt         60
cgagctctga ggagagcccc cgcttctacc cgcgcctctt cccggcagcc gaaccccaaa        120
cagccacccg ccaggatgcc gcctcctcac tcacccactc gccaccgcct gcgcctccgc        180
cgccgcgggc gcaggcaccg caaccgcagc ccgcccccgg gccgcccccc gggccgcc          240 cgaccacgcc ccggccccgg ccccggcccc tagcgcgcga ctcctgagtt ccagagcttg        300
ctacaggctg cggttgtttc cctccttgtt ttcttctggt taatcttat  caggtctttt        360 cttgttcacc ctcagcgagt actgtgagag caagtagtgg ggagagggg  tgggaaaaac        420 aaaaacacac acctcctaaa cccacacctg ctcttgctag accccgcccc caaaagagaa        480
gcaaccgggc agcagggacg gctgacacac aagcgtcat  ctttacgtg  gcggaacttt       540 gtcgctgttt gacgcacctc tctttcctag cgggacaccg taggttacgt ctgtctgttt       600
```

```
tctatgtgcg atgacgtttt ctcacgaggc tagcgaaatg gggcggggca            650
```

<210> SEQ ID NO 9
<211> LENGTH: 287
<212> TYPE: DNA
<213> ORGANISM: Artificial Sequence
<220> FEATURE:
<223> OTHER INFORMATION: Synthetic

<400> SEQUENCE: 9

```
aagaaaacaa ggagggaaac aaccgcagcc tgtagcaagc tctggaactc aggagtcgcg    60
cgctaggggc cggggccggg gcgtggtcgg ggcgggcccg ggggcgggcc cggggcgggg   120
ctgcggttgc ggtgcctgcg cccgcggcgg cggaggcgca ggcggtggcg agtgggtgag   180
tgaggaggcg gcatcctggc gggtggctgt ttggggttcg gctgccggga agaggcgcgg   240
gtagaagcgg gggctctcct cagagctcga cgcatttttta ctttccc               287
```

<210> SEQ ID NO 10
<211> LENGTH: 287
<212> TYPE: DNA
<213> ORGANISM: Artificial Sequence
<220> FEATURE:
<223> OTHER INFORMATION: Synthetic

<400> SEQUENCE: 10

```
gggaaagtaa aaatgcgtcg agctctgagg agagccccg cttctacccg cgcctcttcc    60
cggcagccga accccaaaca gccacccgcc aggatgccgc ctcctcactc acccactcgc   120
caccgcctgc gcctccgccg ccgcgggcgc aggcaccgca accgcagccc cgccccgggc   180
ccgccccgg gcccgccccg accacgcccc ggccccggcc cctagcgcgc gactcctgag   240
ttccagagct tgctacaggc tgcggttgtt tccctccttg ttttctt                287
```

<210> SEQ ID NO 11
<211> LENGTH: 230
<212> TYPE: DNA
<213> ORGANISM: Artificial Sequence
<220> FEATURE:
<223> OTHER INFORMATION: Synthetic

<400> SEQUENCE: 11

```
aagaaaacaa ggagggaaac aaccgcagcc tgtagcaagc tctggaactc aggagtcgcg    60
cgctaggggc cggggccggg gcgtggtcgg ggcgggcccg ggggcgggcc cggggcgggg   120
ctgcggttgc ggtgcctgcg cccgcggcgg cggaggcgca ggcggtggcg agtgggtgag   180
tgaggaggcg gcatcctggc gggtggctgt ttggggttcg gctgccggga               230
```

<210> SEQ ID NO 12
<211> LENGTH: 35
<212> TYPE: DNA
<213> ORGANISM: Artificial Sequence
<220> FEATURE:
<223> OTHER INFORMATION: Synthetic

<400> SEQUENCE: 12

```
aagaaaacaa ggagggaaac aaccgcagcc tgtaa                              35
```

<210> SEQ ID NO 13
<211> LENGTH: 34
<212> TYPE: DNA
<213> ORGANISM: Artificial Sequence
<220> FEATURE:
<223> OTHER INFORMATION: Synthetic

<400> SEQUENCE: 13
aagaaaacaa ggagggaaac aaccgcagcc tgta                                    34

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
gaacaggtac ttctcagtga tgg                                               23

<210> SEQ ID NO 15
<211> LENGTH: 360
<212> TYPE: DNA
<213> ORGANISM: Artificial Sequence
<220> FEATURE:
<223> OTHER INFORMATION: Synthetic

<400> SEQUENCE: 15
ggctccaaag acagaacagg tacttctcag tgatggagaa ataacttttc ttgccaacca       60
cactctaaat ggagaaatcc ttcgaaatgc agagagtggt gctatagatg taaagttttt      120
tgtcttgtct gaaaagggag tgattattgt ttcattaatc tttgatggaa actggaatgg      180
ggatcgcagc acatatggac tatcaattat acttccacag acagaactta gtttctacct      240
cccacttcat agagtgtgtg ttgatagatt aacacatata atccggaaag gaagaatatg      300
gatgcataag gtaagtgatt tttcagctta ttaatcatgt taacctatct gttgaaagct      360

<210> SEQ ID NO 16
<211> LENGTH: 360
<212> TYPE: DNA
<213> ORGANISM: Artificial Sequence
<220> FEATURE:
<223> OTHER INFORMATION: Synthetic

<400> SEQUENCE: 16
agctttcaac agataggtta acatgattaa taagctgaaa aatcacttac cttatgcatc       60
catattcttc ctttccggat tatatgtgtt aatctatcaa cacacactct atgaagtggg      120
aggtagaaac taagttctgt ctgtggaagt ataattgata gtccatatgt gctgcgatcc      180
ccattccagt ttccatcaaa gattaatgaa acaataatca ctccctttc agacaagaca       240 aaaaacttta catctatagc accactctct gcatttcgaa ggattctccc atttagagtg      300
tggttggcaa gaaaagttat ttctccatca ctgagaagta cctgttctgt ctttggagcc      360

<210> SEQ ID NO 17
<211> LENGTH: 26
<212> TYPE: DNA
<213> ORGANISM: Artificial Sequence
<220> FEATURE:
<223> OTHER INFORMATION: Synthetic

<400> SEQUENCE: 17
ccttatgcat ccatattctt cctttc                                           26